United States Patent
Anderson

(10) Patent No.: US 8,894,654 B2
(45) Date of Patent: Nov. 25, 2014

(54) DEPTH CONTROLLABLE AND MEASURABLE MEDICAL DRIVER DEVICES AND METHODS OF USE

(75) Inventor: Wayne Anderson, Mammoth Lakes, CA (US)

(73) Assignee: Smart Medical Devices, Inc., Mammoth Lakes, CA (US)

(*) Notice: Subject to any disclaimer, the term of this patent is extended or adjusted under 35 U.S.C. 154(b) by 594 days.

(21) Appl. No.: 13/077,794

(22) Filed: Mar. 31, 2011

(65) Prior Publication Data

US 2011/0245833 A1 Oct. 6, 2011

Related U.S. Application Data

(60) Provisional application No. 61/319,771, filed on Mar. 31, 2010, provisional application No. 61/333,685, filed on May 11, 2010, provisional application No. 61/421,596, filed on Dec. 9, 2010.

(51) Int. Cl.
| | |
|---|---|
| A61B 17/16 | (2006.01) |
| B23B 49/02 | (2006.01) |
| B23B 45/00 | (2006.01) |
| B25B 23/00 | (2006.01) |
| B25B 21/00 | (2006.01) |
| A61B 17/00 | (2006.01) |
| A61B 17/88 | (2006.01) |
| A61B 19/00 | (2006.01) |
| A61B 10/02 | (2006.01) |
| A61B 17/80 | (2006.01) |
| A61B 17/15 | (2006.01) |
| A61B 17/17 | (2006.01) |
| A61B 17/84 | (2006.01) |

(52) U.S. Cl.
CPC ....... *A61B 17/17* (2013.01); *A61B 2017/00022* (2013.01); *A61B 17/1626* (2013.01); *A61B 17/8875* (2013.01); *A61B 2017/00734* (2013.01); *A61B 17/1628* (2013.01); *B23B 2260/062* (2013.01); *A61B 17/1633* (2013.01); *B23B 49/02* (2013.01); *A61B 17/1631* (2013.01); *A61B 2019/464* (2013.01); *B23B 45/008* (2013.01); *A61B 10/025* (2013.01); *A61B 2017/00119* (2013.01); *A61B 17/80* (2013.01); *A61B 2017/00128* (2013.01); *A61B 2017/00371* (2013.01); *B25B 23/0064* (2013.01); *A61B 17/15* (2013.01); *A61B 2017/00199* (2013.01); *A61B 17/8861* (2013.01); *A61B 10/0283* (2013.01); *B25B 21/002* (2013.01); *A61B 17/1728* (2013.01); *A61B 2017/00991* (2013.01); *A61B 17/848* (2013.01); *A61B 2019/304* (2013.01); *A61B 2019/306* (2013.01); *A61B 2019/462* (2013.01); *A61B 17/1615* (2013.01); *A61B 19/2203* (2013.01); *A61B 17/1624* (2013.01)
USPC .............................. 606/80; 173/176; 173/181

(58) Field of Classification Search
USPC .......... 606/79, 80, 96; 408/8–11, 16, 97, 102, 408/202; 173/2, 4, 11, 176, 181, 217; 73/862.193; 318/432, 461–465
See application file for complete search history.

(56) References Cited

U.S. PATENT DOCUMENTS

| | | | |
|---|---|---|---|
| 3,397,600 A | * | 8/1968 | Wells ............................ 408/112 |
| 3,854,836 A | | 12/1974 | Weissman |

(Continued)

FOREIGN PATENT DOCUMENTS

| | | |
|---|---|---|
| JP | 1984196105 A | 11/1984 |
| WO | WO 97/24991 | 7/1997 |

(Continued)

OTHER PUBLICATIONS http://www.motion-control-info.com/encoder_design_guide.html.

*Primary Examiner* — Todd Manahan
*Assistant Examiner* — Eric S Gibson
(74) *Attorney, Agent, or Firm* — Fred C. Hernandez; Mintz Levin Cohn Ferris Glovsky and Popeo, P.C.

(57) ABSTRACT

Disclosed is a medical driving device having a first motor coupled to a region of a first drive shaft; a second motor coupled to a second drive shaft; a coupler coupled to the second drive shaft and interchangeably connected to a working tool; a tool guide assembly comprising a tool guide surrounding the working tool and a surface guide having a distal region configured to couple to the tool guide and a proximal region configured to couple to the first motor, wherein the first motor causes axial motion of the tool guide assembly to a retracted state and drives a length of the working tool into a target region of a bone; a torque sensor configured to sense torque in at least the second motor by continuously measuring current used to drive the second motor; and programmable electronics package to keep RPMs constant. Related methods, systems, and/or articles are described.

29 Claims, 16 Drawing Sheets

(56) References Cited

U.S. PATENT DOCUMENTS

| | | |
|---|---|---|
| 3,867,932 A | 2/1975 | Huene et al. |
| 4,005,527 A | 2/1977 | Wilson et al. |
| 4,209,069 A * | 6/1980 | Smith ............................ 173/75 |
| 4,242,017 A | 12/1980 | De Fazio |
| 4,341,206 A | 7/1982 | Perrett et al. |
| 4,351,467 A | 9/1982 | White |
| 4,461,015 A | 7/1984 | Kulhavy |
| 4,601,518 A | 7/1986 | Laneus |
| 4,620,539 A | 11/1986 | Andrews et al. |
| 4,688,970 A * | 8/1987 | Eckman ............................ 408/9 |
| 4,710,075 A | 12/1987 | Davison |
| 4,723,911 A | 2/1988 | Kurtz |
| 4,854,873 A | 8/1989 | Linden |
| 4,961,674 A | 10/1990 | Wang et al. |
| 5,405,348 A | 4/1995 | Anspach, Jr. et al. |
| 5,409,493 A | 4/1995 | Greenberg |
| 5,411,503 A * | 5/1995 | Hollstien et al. ............ 606/86 R |
| 5,454,811 A | 10/1995 | Huebner |
| 5,538,423 A * | 7/1996 | Coss et al. ........................ 433/27 |
| 5,554,154 A | 9/1996 | Rosenberg |
| 5,569,254 A | 10/1996 | Carlson et al. |
| 5,575,793 A | 11/1996 | Carls et al. |
| 5,613,810 A | 3/1997 | Bureller |
| 5,653,712 A | 8/1997 | Stern |
| 5,667,509 A | 9/1997 | Westin |
| 5,669,915 A | 9/1997 | Caspar et al. |
| 5,755,537 A | 5/1998 | Lubbering |
| 5,755,721 A | 5/1998 | Hearn |
| 5,810,821 A | 9/1998 | Vandewalle |
| 5,833,404 A * | 11/1998 | Johnson et al. ............... 408/130 |
| 5,875,920 A | 3/1999 | Parent |
| 5,890,897 A | 4/1999 | Kruger et al. |
| 5,895,389 A | 4/1999 | Schenk et al. |
| 5,941,706 A | 8/1999 | Ura |
| 5,961,257 A * | 10/1999 | Bettini et al. .................... 408/97 |
| 5,993,453 A | 11/1999 | Bullara et al. |
| 5,993,454 A | 11/1999 | Longo |
| 5,997,541 A | 12/1999 | Schenk |
| 6,022,352 A | 2/2000 | Vandewalle |
| 6,022,356 A | 2/2000 | Noyes et al. |
| 6,033,409 A * | 3/2000 | Allotta ............................ 606/80 |
| 6,096,042 A * | 8/2000 | Herbert ............................ 606/80 |
| 6,096,051 A | 8/2000 | Kortenbach et al. |
| 6,146,385 A | 11/2000 | Torrie et al. |
| 6,171,312 B1 | 1/2001 | Beaty |
| 6,209,886 B1 | 4/2001 | Estes et al. |
| 6,238,400 B1 | 5/2001 | Bays |
| 6,277,135 B1 | 8/2001 | Wang |
| 6,337,142 B2 | 1/2002 | Harder et al. |
| 6,342,057 B1 | 1/2002 | Brace et al. |
| 6,379,364 B1 | 4/2002 | Brace et al. |
| 6,391,016 B2 | 5/2002 | Bays |
| 6,416,517 B2 | 7/2002 | Harder et al. |
| 6,436,103 B1 | 8/2002 | Suddaby |
| 6,514,018 B2 | 2/2003 | Martinez et al. |
| 6,547,562 B2 | 4/2003 | Kumar |
| 6,565,293 B2 * | 5/2003 | Desmoulins ..................... 408/10 |
| 6,605,092 B2 | 8/2003 | Grumberg et al. |
| 6,610,067 B2 | 8/2003 | Tallarida et al. |
| 6,635,060 B2 | 10/2003 | Hanson et al. |
| 6,645,227 B2 | 11/2003 | Fallin et al. |
| 6,665,948 B1 | 12/2003 | Kozin et al. |
| 6,702,818 B2 | 3/2004 | Kupferschmid et al. |
| 6,776,562 B2 * | 8/2004 | Morrison et al. ............... 408/56 |
| 6,786,683 B2 | 9/2004 | Schaer et al. |
| 6,849,071 B2 | 2/2005 | Whitman et al. |
| 6,872,036 B2 * | 3/2005 | Linderholm .................. 409/200 |
| 6,925,725 B2 | 8/2005 | Herrmann et al. |
| 6,951,562 B2 | 10/2005 | Zwirnmann |
| 6,974,481 B1 | 12/2005 | Carson |
| 7,004,943 B2 | 2/2006 | Ferrante et al. |
| 7,011,661 B2 | 3/2006 | Riedel et al. |
| 7,021,933 B2 | 4/2006 | Caldwell |
| 7,033,363 B2 | 4/2006 | Powell |
| 7,048,477 B2 | 5/2006 | Abrams |
| 7,066,940 B2 | 6/2006 | Riedel et al. |
| 7,073,989 B2 * | 7/2006 | Erickson et al. ................ 408/97 |
| 7,081,119 B2 | 7/2006 | Stihl |
| 7,094,242 B2 | 8/2006 | Ralph et al. |
| 7,108,459 B1 | 9/2006 | Mueller |
| 7,111,411 B2 | 9/2006 | Knopfle et al. |
| 7,150,751 B2 | 12/2006 | Lechot |
| 7,163,542 B2 | 1/2007 | Ryan |
| 7,179,259 B1 | 2/2007 | Gibbs |
| 7,188,431 B2 | 3/2007 | Herrmann et al. |
| 7,210,881 B2 | 5/2007 | Greenberg |
| 7,226,450 B2 | 6/2007 | Athanasiou et al. |
| 7,258,692 B2 | 8/2007 | Thelen et al. |
| 8,529,567 B2 * | 9/2013 | Garcia et al. .................... 606/80 |
| 2003/0049082 A1 | 3/2003 | Morrison et al. |
| 2003/0143042 A1 | 7/2003 | Doyle et al. |
| 2003/0229354 A1 | 12/2003 | Schmieding et al. |
| 2003/0233098 A1 | 12/2003 | Markworth |
| 2004/0049128 A1 | 3/2004 | Miller et al. |
| 2004/0059317 A1 | 3/2004 | Hermann |
| 2004/0146367 A1 * | 7/2004 | Gerhardt et al. ............... 408/110 |
| 2004/0179910 A1 | 9/2004 | Theising et al. |
| 2004/0215395 A1 | 10/2004 | Strasser et al. |
| 2004/0265082 A1 | 12/2004 | Abrams |
| 2005/0116673 A1 * | 6/2005 | Carl et al. ....................... 318/432 |
| 2005/0131415 A1 * | 6/2005 | Hearn et al. ..................... 606/80 |
| 2005/0169717 A1 | 8/2005 | Field |
| 2006/0085005 A1 | 4/2006 | Kenealy, III et al. |
| 2006/0104731 A1 | 5/2006 | Etter et al. |
| 2006/0106363 A1 | 5/2006 | Aravena et al. |
| 2006/0217729 A1 * | 9/2006 | Eskridge et al. ................ 606/80 |
| 2006/0224161 A1 | 10/2006 | Bhattacharyya |
| 2006/0241628 A1 | 10/2006 | Parak |
| 2006/0269372 A1 | 11/2006 | Goshima |
| 2007/0217879 A1 | 9/2007 | Larsson |
| 2009/0196696 A1 * | 8/2009 | Otsuka et al. ..................... 408/6 |
| 2009/0245956 A1 | 10/2009 | Apkarian et al. |
| 2009/0297284 A1 * | 12/2009 | Brown et al. ..................... 408/3 |
| 2009/0326537 A1 | 12/2009 | Anderson |
| 2010/0160924 A1 * | 6/2010 | Soliman ........................... 606/96 |

FOREIGN PATENT DOCUMENTS

| | | |
|---|---|---|
| WO | WO 2004/019785 | 3/2004 |
| WO | WO 2009/158115 | 12/2009 |

* cited by examiner

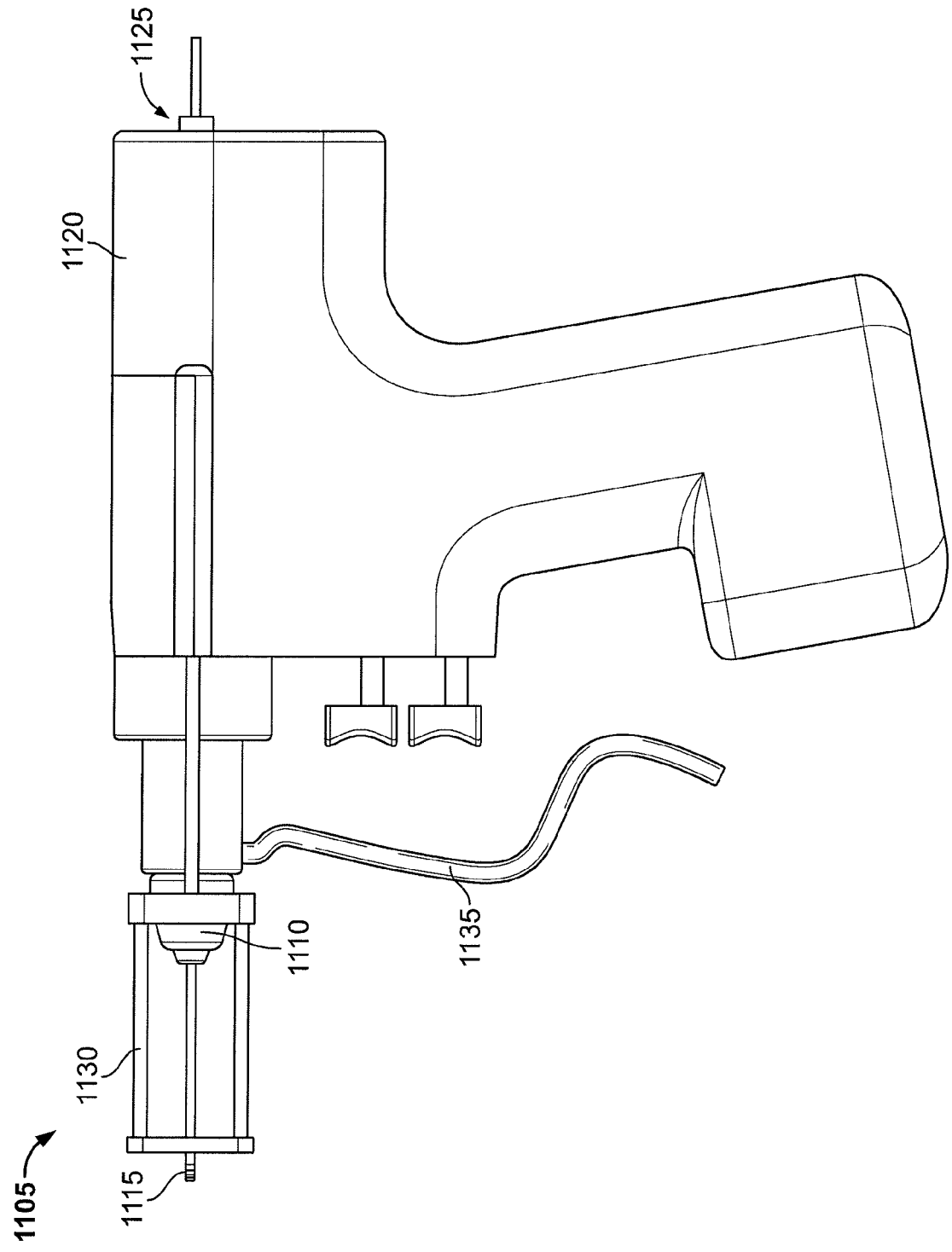

DEPTH CONTROLLABLE AND MEASURABLE MEDICAL DRIVER DEVICES AND METHODS OF USE

REFERENCE TO PRIORITY DOCUMENTS

This application claims the benefit of priority to U.S. Provisional Patent Application Ser. No. 61/319,771, filed on Mar. 31, 2010; and U.S. Provisional Patent Application Ser. No. 61/333,685, filed on May 11, 2010; and U.S. Provisional Patent Application Ser. No. 61/421,596, filed on Dec. 9, 2010. Priority of the filing dates and the disclosures of the Provisional patent applications are hereby incorporated by reference in their entirety.

BACKGROUND

Orthopedic surgery can require bone drilling for the repair of fractures or insertion of implants or other devices. The resulting holes can be used to accept screws, implants and other devices to exert pressure, fixation or reduction of the bone or to place prosthetic joints or other implants. Other medical procedures can require access to bone. For example, the interosseous canal of bone can be accessed to allow fluid administration. Bone can also be accessed to allow the harvesting of bone, collection of bone marrow cores, or for the aspiration of bone marrow for diagnostic or therapeutic purposes. During any procedure where a drill or other driver is used to advance a tool into and through bone, the user must consciously and carefully limit the penetration to the desired depth. If the user allows the tool to penetrate further, the patient can suffer injury to distal structures such as nerve, brain, spinal cord, artery, vein, muscle, fascia, bone or joint space structures. These types of injuries can lead to severe patient morbidity and even death. The devices inserted to a drilled bore often must fit within a narrow length range that can vary sometimes by no more than a millimeter or less.

Once the drilling of a bone is safely complete, it is often prudent to obtain the depth of the bore made by the drilling tool. Many procedures require knowledge of the depth of tool penetration, such as in the placement of internal fixation devices, screws and other implantable hardware. Selecting an appropriate length of the screw or other implant necessary for the procedure depends upon such knowledge of the bore's depth. Conventional techniques used in the art are often inconvenient, time consuming and unreliable often requiring trial and error and multiple exposures to radiographs before the proper implant insertion is achieved.

A common way to obtain the depth of the bore formed by a drilling tool is to use a depth gauge. Often users must interrupt the drilling procedure in order to palpate or measure with a depth gauge whether or not the desired depth has been achieved. In many instances a user will take a radiograph during a drilling procedure to confirm the appropriate depth of penetration has been achieved or take a radiograph while the depth gauge is in place to ensure the information the gauge provides is accurate. Depth gauges used in the art can be inaccurate resulting in a user placing a screw of an inappropriate length not often identified until a confirming radiograph is taken. Each radiograph taken increases the radiation exposure of the surgeon, staff and patient in the operating suite. Depth gauges known in the art can also break and require the user to retrieve it from the bore. Inconvenient and inaccurate depth measurement devices and methods can result in improperly sized screws that must be removed and replaced with new properly sized screws. Wasted hardware, increased disruptions and delays in orthopedic procedures ultimately increase the expense of a procedure as well as expose the surgeon, staff and the patient to unnecessary radiation. The cost of the additional time, the wasted hardware and the radiation exposure are quite significant.

SUMMARY

The techniques known in the art to drill holes in bone are technically demanding and require separate measuring steps that interrupt the actual drilling of the bone adding time, cost and the need for additional confirming radiographs to complete such procedures. There remains a need for safer, controlled drilling methods and devices. There is also a need for an instrument that simultaneously controls and measures the depth of penetration of the instrument during procedures such as placement of internal fixation devices, screws, and other implantable hardware.

In one aspect, disclosed is a medical driving device including a housing having a proximal end and a distal end. The housing includes a hand-held portion near the proximal end of the housing; and an engagement portion near the distal end of the housing; a first drive shaft extending through a region of the housing between the proximal and distal ends; a first drive element coupled to a region of the first drive shaft; a second drive element coupled to the first drive shaft and to a second drive shaft; a coupler coupled to the second drive element, the coupler interchangeably connected to a working tool; and a tool guide assembly. The tool guide assembly includes a tool guide surrounding the working tool; a forward surface guide having a proximal region and a distal region, the distal region configured to couple to the tool guide; and a rear surface guide configured to couple to the first drive shaft and the proximal region of the forward surface guide. The device further includes a programmable electronics package configured to sense torque in at least the second drive element.

The first drive shaft and the second drive shaft can be in a co-axial arrangement, parallel arrangement, or an orthogonal co-axial arrangement relative to one another. The hand-held portion further can include an actuator. The second drive element coupled to the second drive shaft can drive the coupler and the working tool. The coupler and the working tool can be rotated by the second drive shaft. The coupler and the working tool can be oscillated by the second drive shaft. The tool guide assembly can travel axially towards the proximal end of the housing to a retracted state upon actuation of the first drive shaft. Axial travel of the tool guide towards the proximal end of the housing can reveal a length of the working tool that extends beyond the tool guide. The working tool can be a drill bit, a detuned drill bit, wire, Kirschner wire, pin, trochar, burr, screwdriver, reamer, saw, saw blade, router, router bit, stepped drill bit, bone plug removal tool, bone harvesting tool, bone marrow harvesting tool, and bone marrow aspirating tool. The programmable electronics package can measure current used to drive the second drive element. The current measured can correspond to a torque of the working tool and the material strength and density of work penetrated. The device can further include a torque sensor positioned on the housing between the second drive element and the working tool, the torque sensor configured to directly measure torque of the working tool. The torque sensor can be configured to communicate measurements of torque to the programmable electronics package. A change in the measurements of torque can correspond to change in material strength and density of work penetrated.

The device can further include an alert such that the torque sensor communicates with the programmable electronics package in real-time and the alert provides a user with information regarding status of the driving device during use. The alert can be an auditory, visual or tactile signal. The work penetrated can be medullary canal, cancellous bone, cortical bone, or soft tissue. The device can further include one or more axial force sensors configured to sense the axial force applied at one or both of the distal end of the tool guide and the working tool. The device can further include an axial force alert, the axial force sensor communicates with the programmable electronics package in real-time and the axial force alert provides a user with information regarding status of the driving device during use. The axial force alert can be an auditory, visual or tactile signal. The visual signal can be one or more LEDs positioned within a user line-of-sight, wherein the LEDs indicate degree of axial pressure being applied by the user in real-time. The proximal region of the forward surface guide can be telescopically coupled to the rear surface guide. The device can further include a gearbox connecting the second drive element to the working tool. The tool guide surrounding the working tool can be configured to assist in the engagement of an implant. The tool guide can include one or more features that mechanically couple with corresponding features of the implant. The implant can be a fracture fixation plate or a joint part. The tool guide can couple to the implant at an angle away from perpendicular.

In another aspect, disclosed is a method of penetrating bone using a driving instrument including contacting a field of bone with a distal engagement end of the instrument; receiving a first input by a first drive element of the instrument, the first drive element coupled to a working tool; driving the working tool at a first speed; receiving a second input by a second drive element of the instrument, the second drive element coupled to a guide surrounding at least a portion of the distal engagement end of the instrument; moving the guide axially in a proximal direction; and revealing a length of the working tool extending beyond the distal engagement end of the instrument.

The length of the working tool extending beyond the distal engagement end of the instrument can correspond to a depth of penetration by the working tool into the field of bone. The method can further include receiving commands by the instrument to electronically program the depth of penetration by the working tool. The method can further include instantaneously measuring axial motion of the guide using a transducer coupled to the instrument. The method can further include adjusting axial movement of the guide to avoid plunge of the working tool. The method can further include adjusting movement of the working tool to avoid tissue damage. The method can further include alerting a user of a change in axial force against the field of bone using a signal, wherein the signal comprises an auditory, visual or tactile signal. The method can further include instantaneously measuring torque of the working tool. The torque can be measured electronically. The torque can be measured directly using a torque sensor in contact with at least a portion of the second drive element. The torque can correspond to a material strength and density of the field of bone. The method can further include alerting a user of a change in material strength and density of the field of bone using a signal, wherein the signal comprises an auditory, visual or tactile signal. A change in torque measured can indicate a transition from a first tissue type to a second tissue type. The first tissue type can include cortical bone and the second tissue type can include medullary canal or cancellous bone. The first tissue type can include medullary canal or cancellous bone and the second tissue type can include cortical bone.

Other features and advantages will be apparent from the following description of various embodiments, which illustrate, by way of example, the principles of the disclosed devices and methods.

BRIEF DESCRIPTION OF THE DRAWINGS

FIG. 12 is a side view of an instrument having a driving tool coupled thereto.

DETAILED DESCRIPTION

This disclosure relates to a surgical instrument for preparing a bore in animal tissue. In an embodiment, the disclosure relates to a surgical instrument that drives a tool in which both drive power and relative axial extension of the tool are controlled and measurable. The instrument can have both a rotational drive and an axial drive, each of which can be controllable by the user. The instrument allows a user to control and simultaneously measure the travel of the tool into a target tissue.

Figure 1:
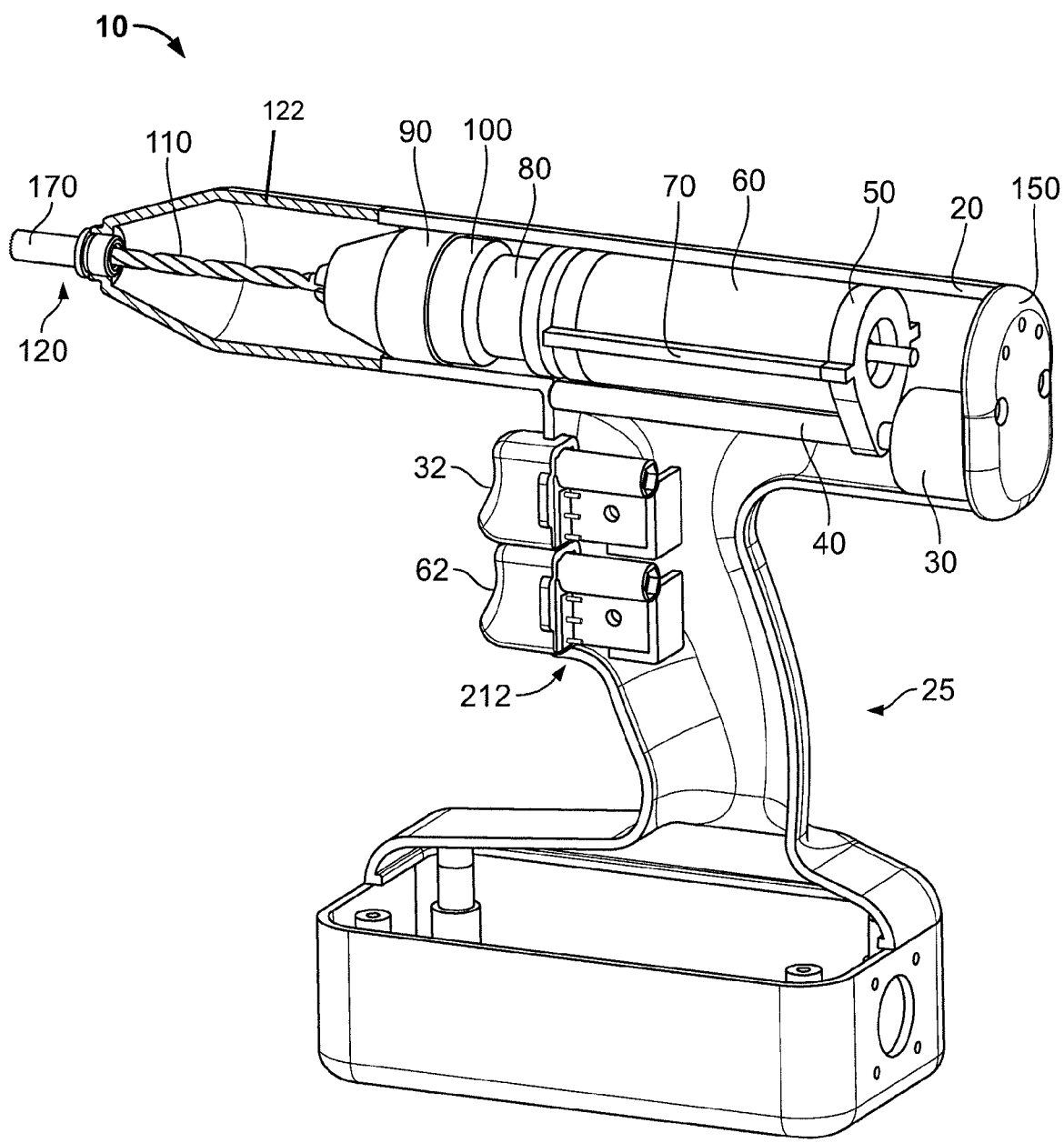
FIG. 1 is a perspective, cut-away view of one embodiment of an instrument.
Figure 2:
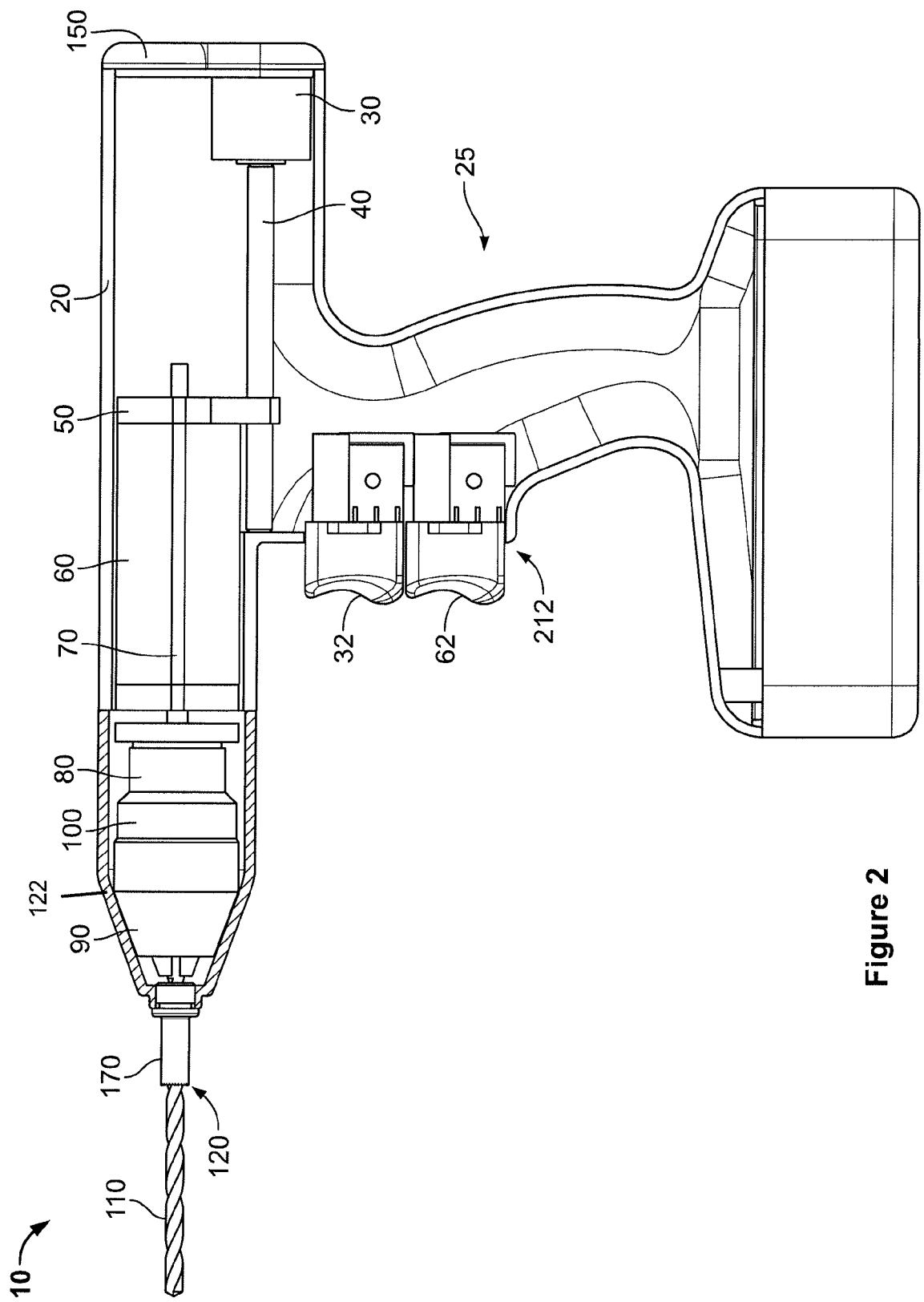
FIG. 2 is a side, cut-away view of the instrument of FIG. 1.

FIGS. 1-2 illustrate cut-away views of an instrument 10. The instrument 10 can include a body 20 that houses two drive motors 30, 60 and a working tool 110 coupled via a chuck 90 extendable near a distal engagement end 120 of the instrument 10. As will be described in more detail below, the instrument 10 can instantaneously sense, meter and control the work created by the tool 110.

Instantaneous sensing, metering and controlling the instrument 10 help to prevent injury to surrounding tissues and structures that could otherwise be caused by the tool 110. For example, sensing, metering and controlling the rotational speed of the drive can reduce the risk of heating surrounding tissue and bone, for example to the point of causing localized burns. Sensing, metering and controlling the axial motion and/or relative extension of the working tool 110 can prevent penetrating injuries, for example, to structures distal of the target such as nerve, brain, spinal cord, artery, vein, muscle, fascia, bone or joint space structures. Instantaneous sensing, metering and controlling the bore created as the working tool penetrates the tissue can provide an advantage when selecting implants for insertion. For example, the length of the drilling hole and subsequently the length of the implant needed can be simultaneously metered upon creating the bore. This eliminates the need for an additional step of measuring the depth of the bore created with a separate device. Further, depth gauges can frequently provide false measurements resulting in users selecting the wrong size implant for insertion and requiring them to remove the implant and reinsert a different sized implant. Conventional depth gauges are also prone to breakage, which can lead to additional time usage and patient morbidity. Sensing, metering and controlling the depth of the bore in real-time or as it is being created eliminates the trial-and-error process of selecting the correct implant for the procedure, which ultimately can improve patient safety.

The instruments described herein also save operating time and the need for additional procedures like repeated radiographs in determining implant size. Because estimates of operating room costs for the personnel alone can be as high as $25 per minute even small savings of time in an operating room can result in large savings of money. The instruments described herein provide an added benefit of reducing the number of radiographs needed in the operating room. Intra-operative radiographs and radiation exposure are one of the major occupational risks to surgeons and operating room staff. Radiation exposure of this type has been shown to lead to radiation dermatitis, cataracts, skin cancers, leukemia and other cancers. The instruments and methods described herein reduce the number of radiographs needed per procedure and the life-time exposure of surgeons and staff to x-rays. This reduced radiation exposure ultimately lowers chronic radiation exposure and the risk of radiation-related illnesses in surgeons and their staff.

Drive System

The configuration of the drive system of the instrument 10 can vary. In an embodiment shown in FIGS. 1-2, drive motor 30 of the instrument 10 can be a fixed axial drive motor 30 and drive motor 60 can be a slidable, rotational drive motor 60. Drive motor 30 can be coupled to a drive shaft 40, which can in turn be coupled to drive motor 60. The drive shaft 40 can be a jack screw, ball screw, lead screw and the like that can translate the torque or rotary movement of the drive motor 30 into thrust in an axial direction to slidably move the drive motor 60 relative to the instrument 10. The drive shaft 40 can be made to move either in a distal (forward) direction or a proximal (reverse) direction that is substantially parallel to the axis of the instrument 10. The drive motor 60 can connect to the drive shaft 40 by way of a detachable coupler 50. The drive motor 60 can be coupled to and rotate a drive shaft 80 that can connect to the chuck 90 that holds the working tool 110. As such, movement of the drive motor 60 along the longitudinal axis of the instrument 10 can cause similar movement of the working tool 110 and extension of the tool 110, for example beyond the distal engagement end 120 of the instrument 10.

In use, the drive shaft 40 driven by drive motor 30 can axially drive the drive motor 60, which can rotate the drive shaft 80, which can rotate the chuck 90 which can rotate the tool 110. The chuck 90 can be stabilized within the body 20, for example by bearings 100. The bearings 100 can be axially slidable and stabilizing. The second drive motor 60 can be constrained or held rotationally still to provide for the eventual rotational movement of the working tool 110. The drive motor 60 can be fixed against rotational movement by guide rails or anti-rotation conducting flanges 70. In an embodiment, the flanges 70 slide within channels in the body 20. In an embodiment, each channel can have an opposite polarity such that they conduct electricity from a power source to the drive motor 60. In another embodiment, the power can be separate from the conducting flanges 70. The anti-rotation conduction flanges 70 can also be spiral shaped and travel through spiral grooves to add stability. The anti-rotation conduction flanges can also be excluded from the device and the rotational drive motor fixed to the axial drive shaft 40 causing the drive motor 60 to turn along with the axial drive shaft 40.

Figure 3:
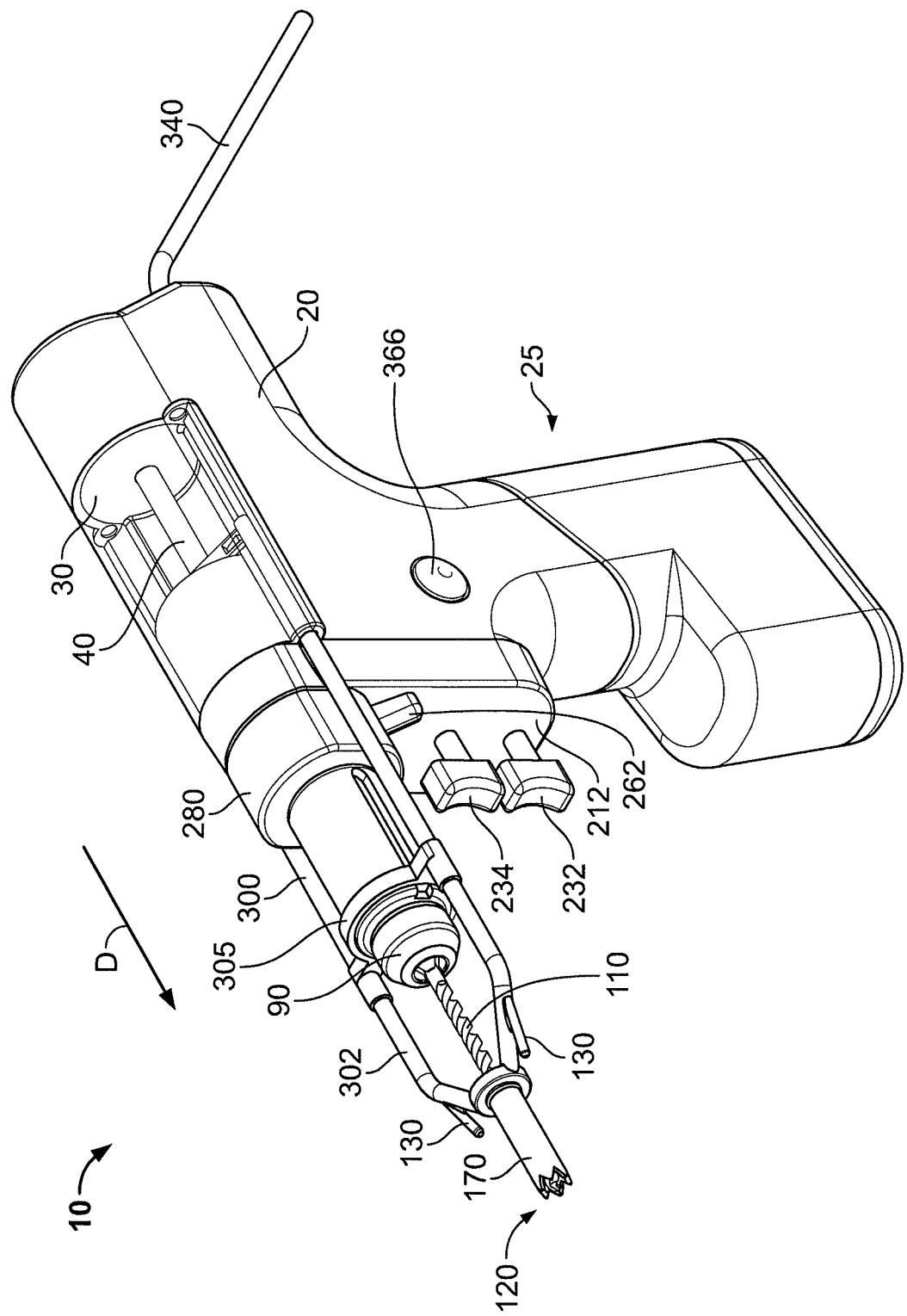
FIG. 3 is a perspective view of another embodiment of an instrument.
Figure 4:
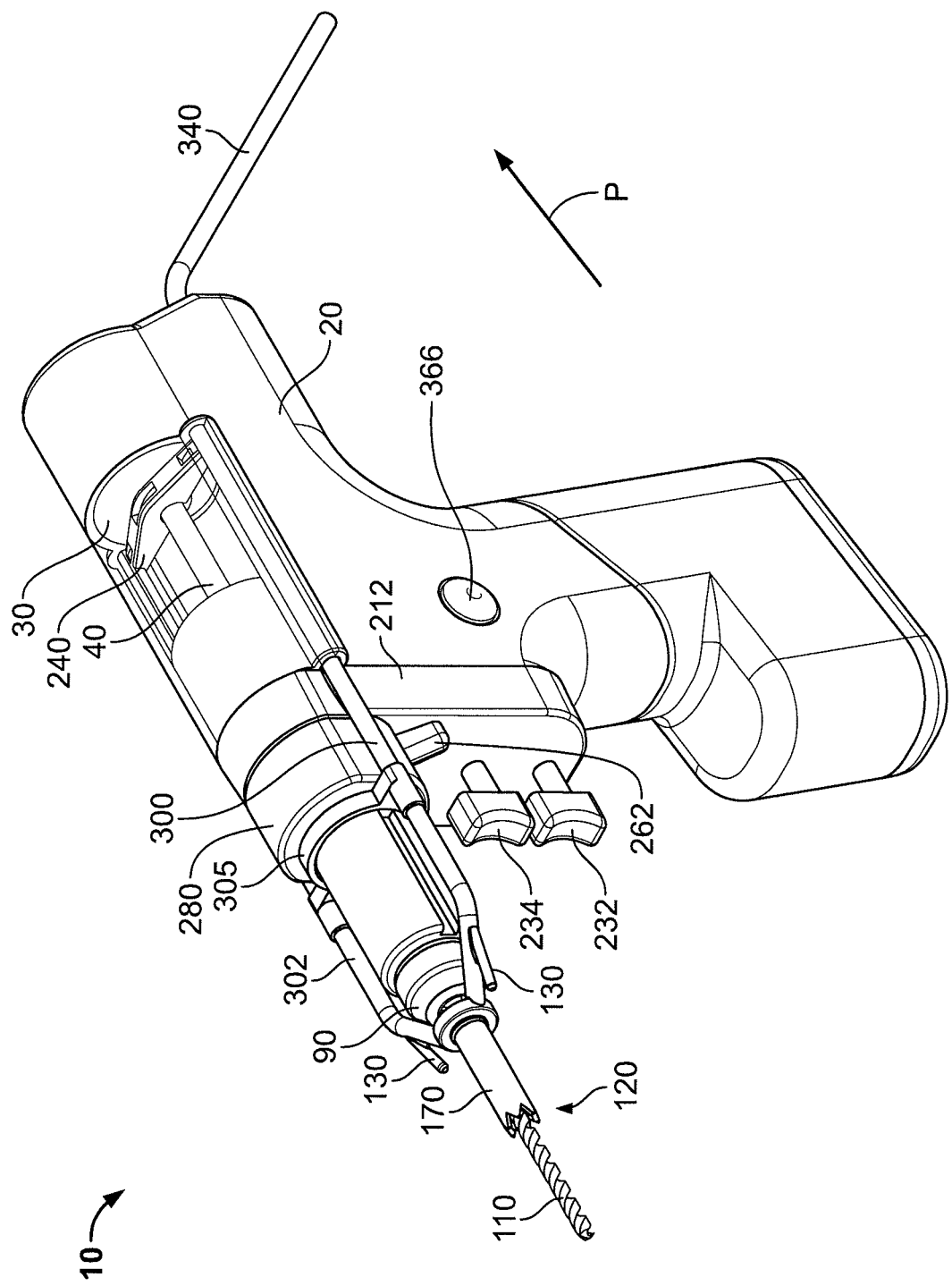
FIG. 4 is a perspective view of the instrument of FIG. 3 showing a length of the working tool in an extended position.
Figure 5:
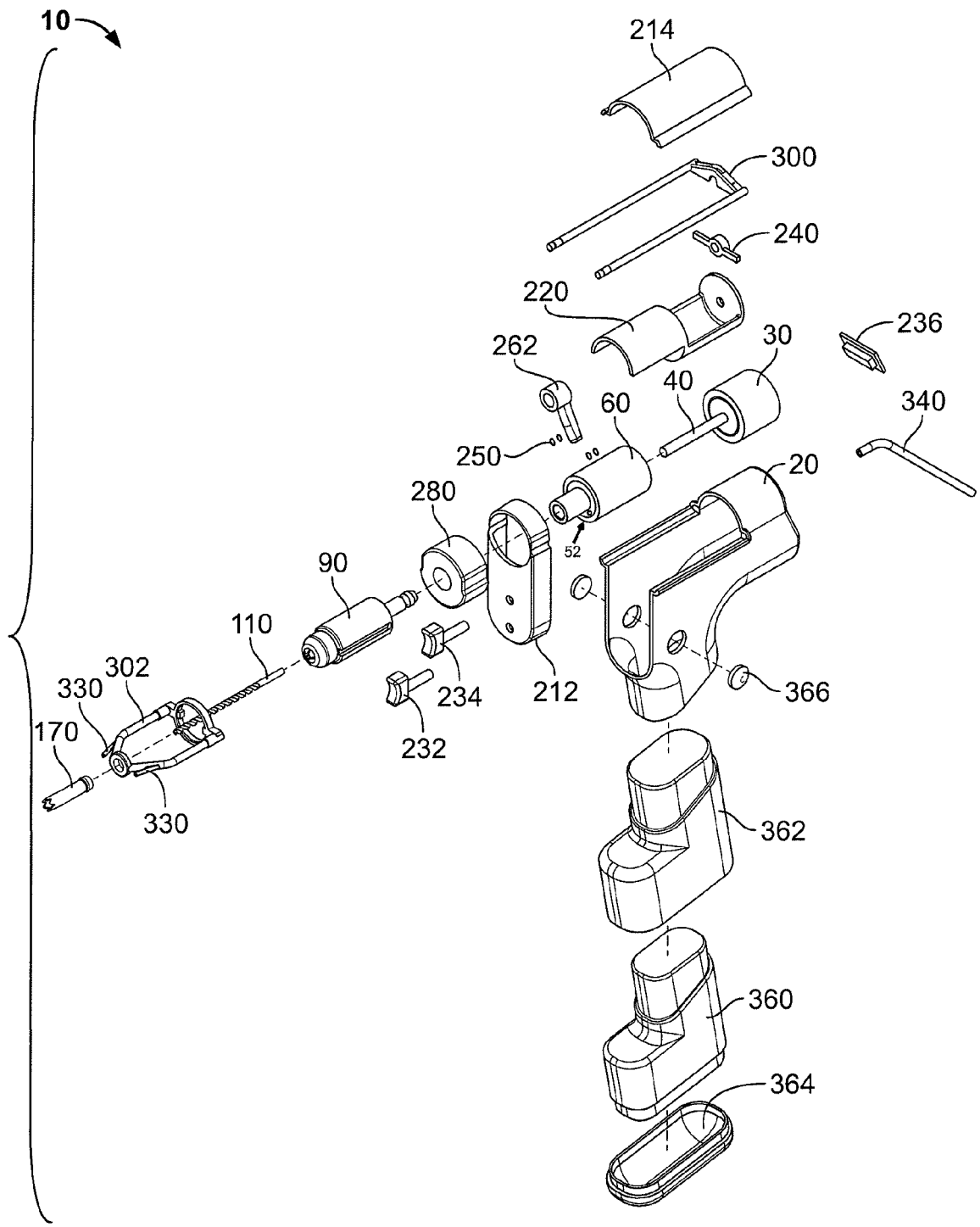
FIG. 5 is an exploded view of the instrument of FIG. 3.
Figure 6:
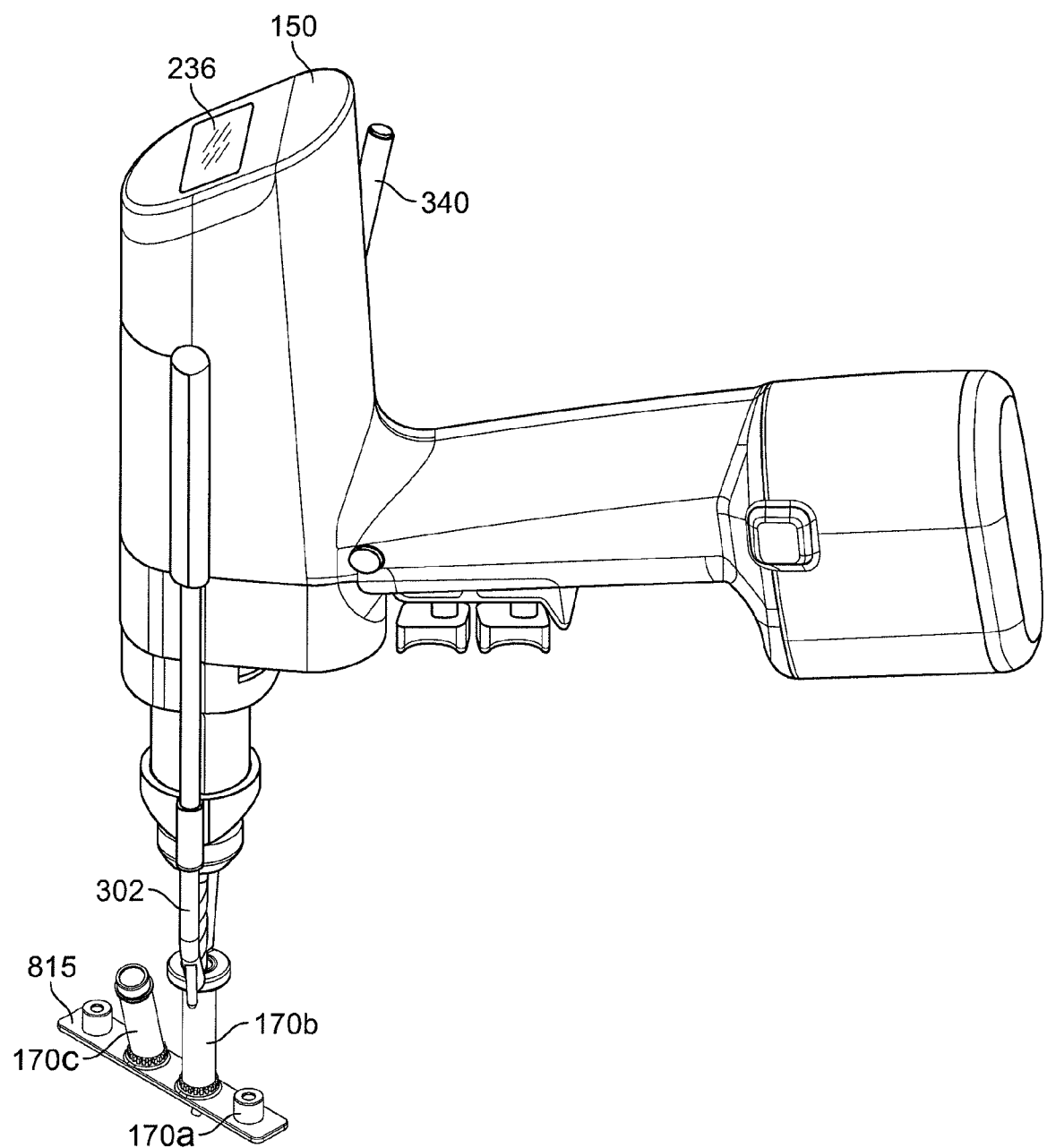
FIG. 6 is a perspective view of an instrument having a guide interfaced with a fracture fixation plate.
Figure 7:
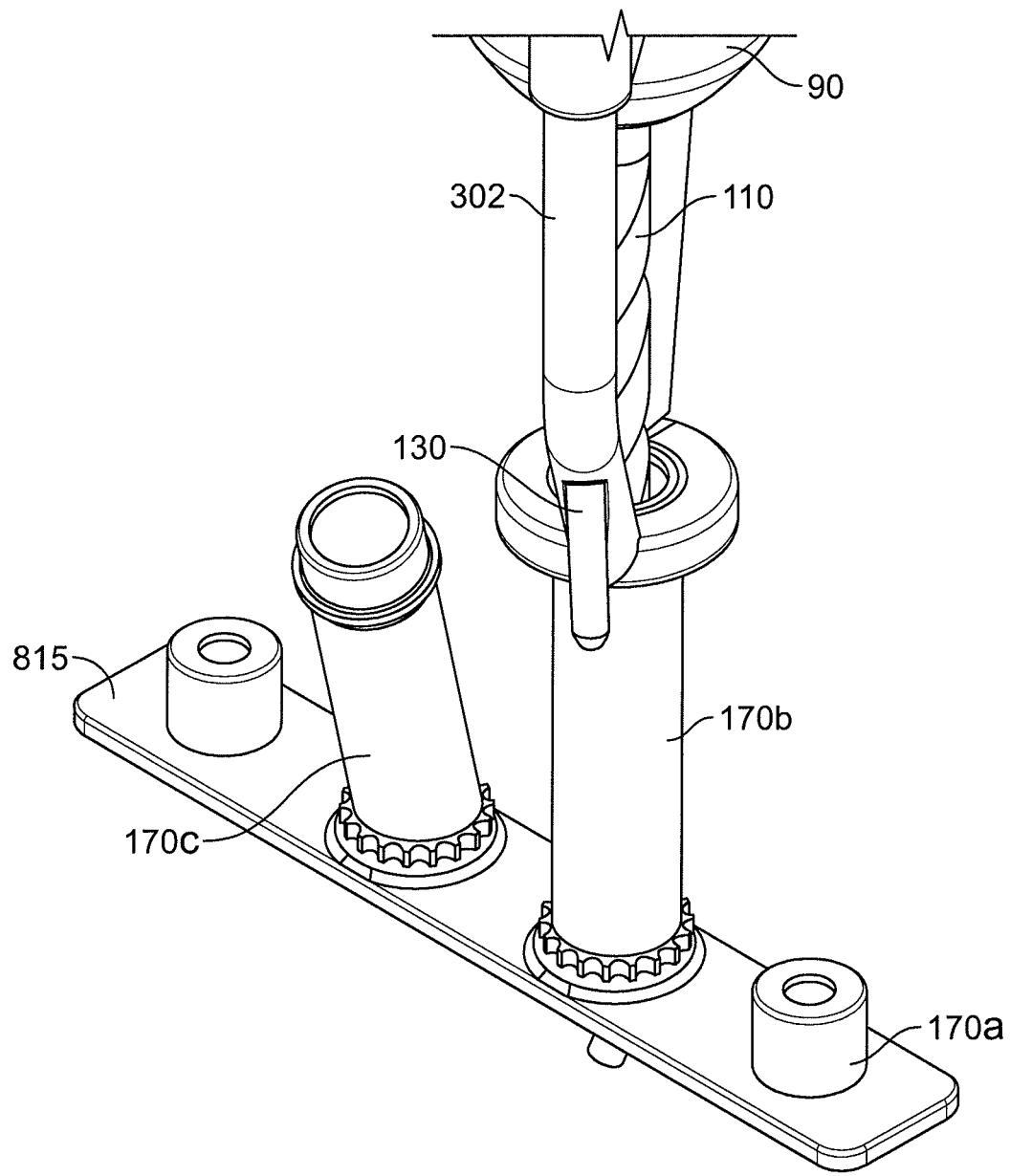
FIG. 7 is a perspective view of the guide of FIG. 6 interfaced with the fracture fixation plate.

It should be appreciated that the configuration of the drive shaft 40, 80 relative to the drive motors 30, 60 can vary. For example, the motors 30, 60 can be in parallel overlapping orientation relative to one another as shown in FIGS. 1 and 2. Alternatively, the drive shaft 40 and motor 30 can be positioned in a co-axial orientation as shown in FIGS. 3, 4 and 5. In another example, the drive shaft 40 and motor 30 can be positioned orthogonal to drive shaft 80 and motor 60. For example, the rotated motor can be positioned within the handle 25 of the instrument 10. The parallel overlapping orientation as well as the orthogonal orientation can provide for a shorter, more compact length of the instrument 10 without limiting the overall extension of the tool 110 that can be achieved. Alternatively, the drive shaft 40, 80 and motor 30, 60 can be connected via a gearbox (not shown).

It should also be appreciated that use of the term "working tool" herein or "rotation of the working tool" is not intended to be limiting and that working tools other than rotating drill bits are considered as will be described in more detail below. Although the embodiments shown herein use motors, such as a stepper motor powered by a battery, it should be appreciated that power systems other than rotational drive motors are considered. For example, a non-electric drive motor, pneumatic motors or actuators powered for example by a nitrogen gas source, electrical motors, hydraulic actuators, and the like or a combination thereof can be incorporated into the instrument. It should also be appreciated that a motor and gearing can be used in place of the two-motor embodiment.

Instrument Guides

Extension of the working tool 110 relative to the longitudinal axis of the instrument 10 can be accomplished as described above via linear movement of the drive motor 60 within the body 20 of the instrument 10. In another embodiment, the drive motor 60 need not move axially relative to the instrument 10. Instead, extension of the working tool 110 relative to the distal engagement end 120 of the instrument 10 can be effected by the movement of one or more surface guides on the instrument 10 as will be described below. FIGS. 3-5 illustrate an embodiment of an instrument 10 that includes a body 20 that houses an axial drive motor 30, a rotational drive motor 60, a working tool 110 coupled via a chuck 90 extendable near a distal engagement end 120 of the instrument 10. A chuck extension 280 can also be included. The instrument 10 can further include a rear surface guide 300 and a forward surface 302 guide that, as will be discussed in more detail below, can be withdrawn in a proximal direction to reveal a length of the working tool 110 extending beyond the distal engagement end 120 of the instrument 10.

The drive motor 30 can be an axial drive motor and spindle seated near the proximal end (rear) of the body 20 and the second drive motor 60 can be a rotational drive motor and spindle seated near the distal (front) end of the body 20. Body insert 220 can fit inside the top of the body 20 such that the body insert 220 covers the drive motors 30, 60 (see FIG. 5). The drive motor 30 can attach to drive a drive shaft 40 and the drive shaft 40 can attach to the drive lug 240. The drive lug 240 can attach to the rear surface guide 300 at its proximal end. The distal end of the rear surface guide 300 can attach to the proximal end of the forward surface guide 302. There can be one or more o-rings 250 between the two surface guides 300, 302. The drive lug 240 and the rear surface guide 300 can sit in the body 20 above the body insert 220. The top of the body 20 also can accept a body cover 214. The rear surface guide 300 can fit between the body 20 and the body cover 214 such that it is free to move within the body 20 and extend beyond the body 20 and the body cover 214.

As best shown in FIG. 3, the forward surface guide 302 can engage an outer surface of the chuck 90, for example, via a sleeve and/or one or more stabilizing flanges 305. In another embodiment, the chuck 90 can function without a sleeve or stabilizing flanges and instead the forward surface guide 302 can have a bushing or other device to engage the chuck 90 directly and still allow the chuck 90 to spin freely.

In use, the axial drive motor 30 can power the drive lug 240 in an axial direction, which in turn can drive in an axial direction the rear surface guide 300 coupled to the forward surface guide 302. An increased length of the working tool 110 is revealed in order to engage the work. The drive motor 60 rotates the chuck 90 and the working tool 110.

The surface guides 300, 302 shown in the drawings have two "arms" or supports that extend axially. But it should be appreciated that the surface guides 300, 302 can have one, two, three or more arms that provide additional support to bear the load. It should also be appreciated that the surface guides 300, 302 can be a single unit. In another embodiment, the surface guides 300, 302 can be telescoping surface guides. This can provide the instrument 10 with a larger range in overall drill length in a more efficient configuration. The telescoping surface guides can each include an actuator such as a pneumatic, hydraulic, motorized or other actuator that causes the surface guides 300, 302 to telescope and change overall guide length (i.e. telescope outward to lengthen or telescope inward to shorten). In another embodiment, the telescoping surface guides 300, 302 can be used to achieve depth control without the use of an axial motor. The axial electric motor can be replaced by a hydraulic or pneumatic motor, as can the rotational motor.

A distal guide 170 can optionally be coupled to the instrument 10. In one embodiment, the distal guide 170 is coupled to a distal end of the body 20 of the instrument 10 (as shown in FIGS. 1 and 2). In another embodiment, the distal guide 170 is coupled to the forward surface guide 302 (as shown in FIGS. 3-5). The distal guide 170 can include a central channel through which the working tool 110 can extend to engage the work. The distal guide 170 can have a tapered geometry or reduced outer diameter such that its contact surface is relatively small compared to the distal end of the body 20 and the bulk of the instrument 10 is focused into a small area of contact with the work. The distal guide 170 can also include gripping features at its forward surface such as spikes or other protrusions such that the guide 170 can hold its position on the work.

The distal guide 170 can assist in the engagement of bone, fracture plates or other implants or joint parts. One or more portions of the distal guide 170 can couple with the implant, for example by directly pressing or screwing the implant onto one or more corresponding features of the distal guide 170. FIGS. 6-9 show an instrument and various embodiments of distal guides 170a, 170b, 170c that can interface with the work using various mechanisms. Guide 170a can engage an implant 815, such as a fracture fixation plate, by a threaded interface, or by another mechanism, such that the guide 170a screws into, or otherwise couples with the implant 815. Guides 170a and 170b are shown connected to the implant 815 in a generally perpendicular configuration. Alternatively, distal guide 170c can connect to the implant 815 at an angle away from perpendicular. The guide 170b can include an interface that provides a unique connection with the implant 815. For example, the distal guide 170b can include a pin-index type connection or a diameter-index type system that provide non-interchangeable connections between the distal guide 170 and the implant 815. As such, a specific implant 815 can interface with a particular distal guide 170 to prevent misconnections.

Figure 8:
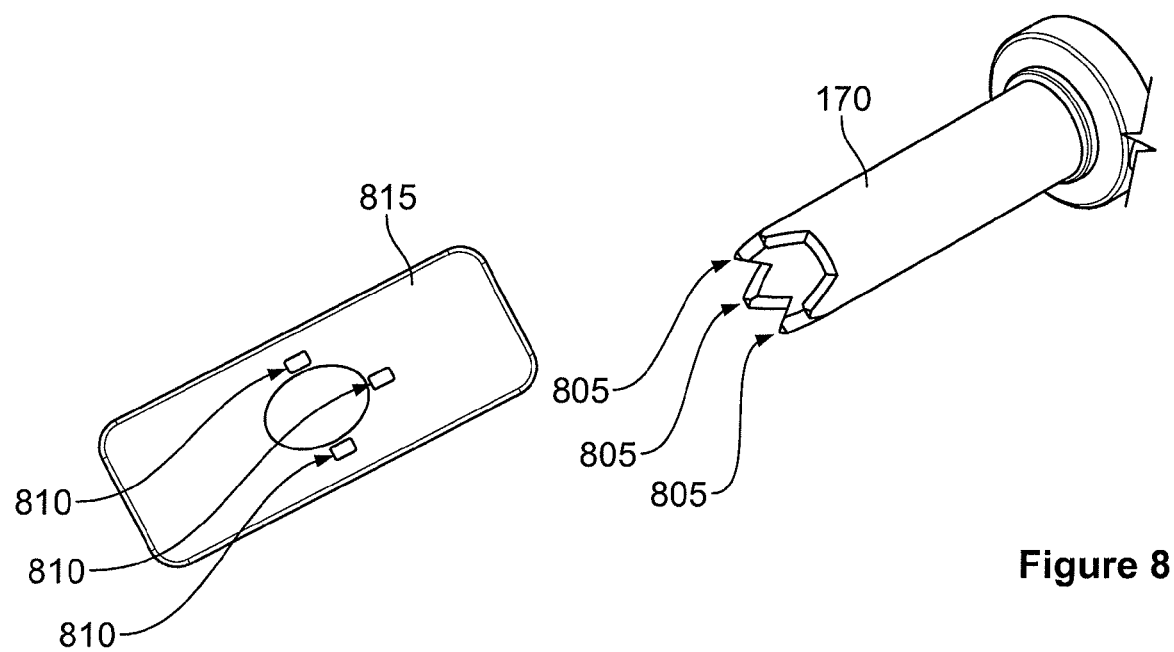
FIG. 8 is a perspective view of a guide/fixation plate interface system.
Figure 9:
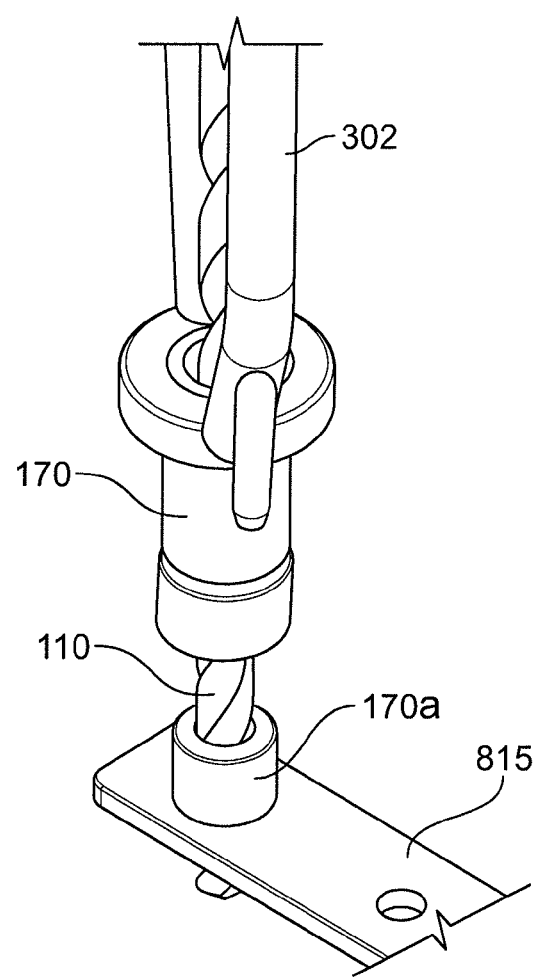
FIG. 9 is a perspective view of a guide coupled to the instrument of FIG. 6 interfaced with the fracture fixation plate.

The specific geometry of the interface between the distal guide 170 and the implant 815 can vary. FIG. 8 shows a schematic of just one example of an interface system between the implant 815 and the distal guide 170. The distal guide 170 can include one or more geometric features 805 that extend from a forward surface of the distal guide 170. The geometric features 805 can couple with corresponding geometric features 810 provided on the implant 815 such that the two properly and uniquely interconnect. The corresponding geometric features 805, 810 can dictate the type of implant 815 that can be used with a particular distal guide 170 providing for a unique pairing between the two. It should be appreciated that although the figure shows the implant 815 as a fracture fixation plate, the implant 815 with which the guide 170 can interface can vary including bone, fracture plates or other implants or joint parts.

The interface between the distal guide 170 and the implant 815 can provide for directional guidance for the working tool 110. The implant 815 can connect to the distal guide 170, the distal guide 170 can connect to the instrument 10 resulting in one interconnected complex for drilling a bore. In one embodiment, the implant 815 couples to the distal guide 170 which can be attached to the instrument 10 via the forward surface guide 302. The implant 815 can also couple a distal guide 170 that is separate from the instrument 10. In another embodiment shown in FIG. 9, the instrument can include two guides. In this embodiment, a first distal guide 170 is attached to the instrument 10 and a second distal guide 170a is connected to the implant 815. The first distal guide 170 can then couple to the second distal guide 170a.

Working Tools

As mentioned above, the working tool 110 can be connected to the instrument 10 using a rotatably-driven coupler or chuck 90 with or without a chuck extension 280. The chuck 90 can be a conventional coupler such as a three-jaw chuck in which the jaws grasp the proximal portion of the tool 110 and hold it firmly in place. The chuck 90 can be actuated to open or close the jaws by a rotation mechanism or a key or other techniques known in the art. The chuck 90 can also be a quick-release type of coupler. The chuck 90 can be extended beyond the distal engagement end 120 such that the chuck 90 can be accessed external of the body 20. This accessibility of the chuck 90 relative to the instrument 10 allows for a user to make reliable connections between the working tool 110 and the chuck 90. The exterior access can also allow for shorter, safer driven tools than if the chuck 90 was internal to the instrument body 20. Additionally, the exterior access can provide for ease of cleaning this portion of the instrument 10.

The working tool 110 as described herein can include, but is not limited to, tools such as a drill bit, Kirschner (or other) wire, pin, trochar, burr, screwdriver, reamer, saw, saw blade, router, router bit, stepped drill bit, bone plug removal tools, bone harvesting tools, bone marrow harvesting tools, bone marrow aspirating tools or any other tools that can be reversibly attached to a chuck 90 or other type of coupling device.

It should be appreciated that where a working tool is described herein as a drill bit or wire or pin or other type of tool that such description is not intended to be limiting. It should be appreciated that a wide variety of tools can be used as the working tool with the instruments described herein. For example, the working tool can be a saw blade connected to a coupler that oscillates or reciprocates the saw blade as described with respect to FIGS. 11A-11B below or a wire driver as described with respect to FIG. 12 below.

The working tool 110 can be made of metal materials such as titanium metal or stainless steel that can be sterilized and reused. Alternatively, the working tool 110 can be made of polymeric material that can be discarded after each use. The material can be chosen to provide the necessary strength to allow the proper tool action.

Figure 10:
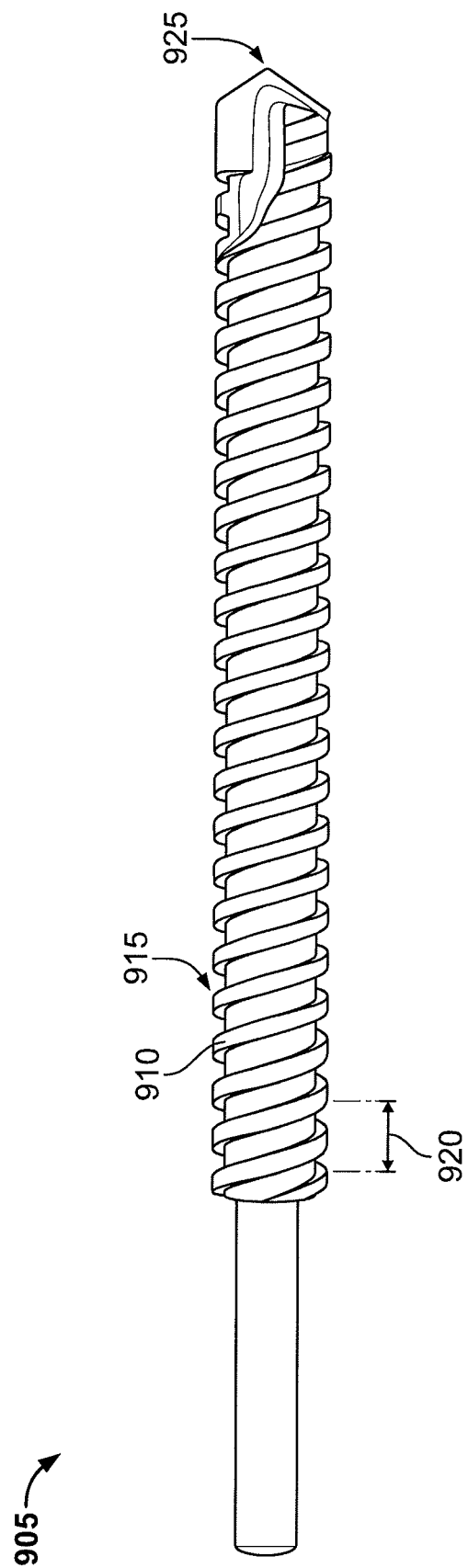
FIG. 10 is a side view of a drill bit having detuned flutes.

FIG. 10 shows an embodiment of a drill bit 905 having a flute 910 that is detuned or dulled. It should be appreciated that the entire length of the flute 910 need not have the same edge geometry. For example, the detuned flute 910 can have an edge 915 that is sharper starting at a proximal region of the bit 905 towards the tool attachment region. It should also be appreciated that the bit 905 can have more than one flute 910 as is known in the art. The detuned flute 910 allows for greater sensitivity in measurement of torque and measurement of current. The bit 905 can also have fast spirals 920 with short rotational diameter and a short tip 925 such that it transfers less energy to the work to avoid over-heating the work and surrounding tissues. The drill bit 905 design also can provide a feel to the user such that information regarding the subtle material strength and density changes of the work can be appreciated during use.

Other Tool Embodiments

Figure 11A:
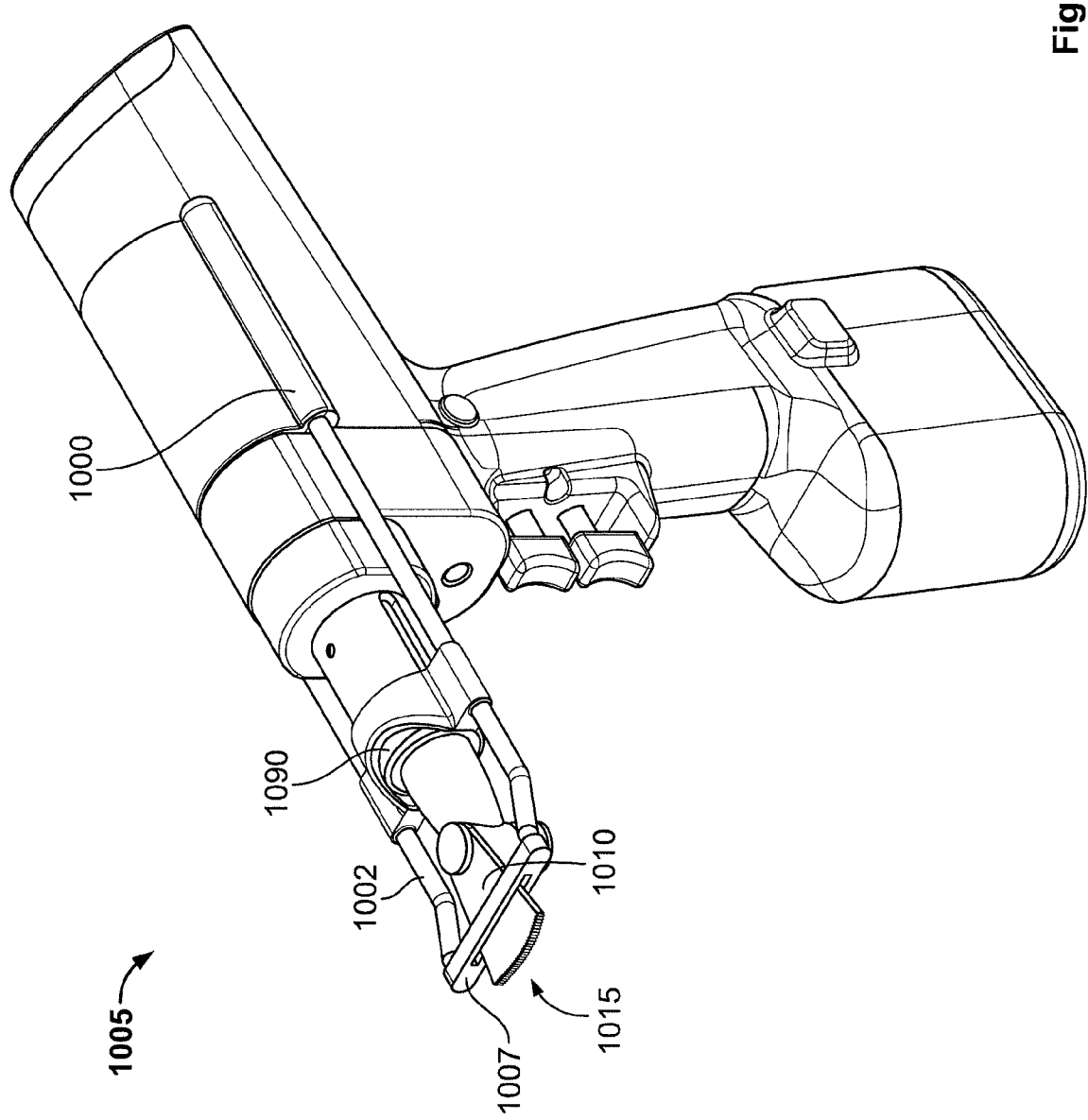
FIGS. 11A and 11B are perspective views of an instrument having a saw blade and saw blade guide coupled thereto.
Figure 11B:
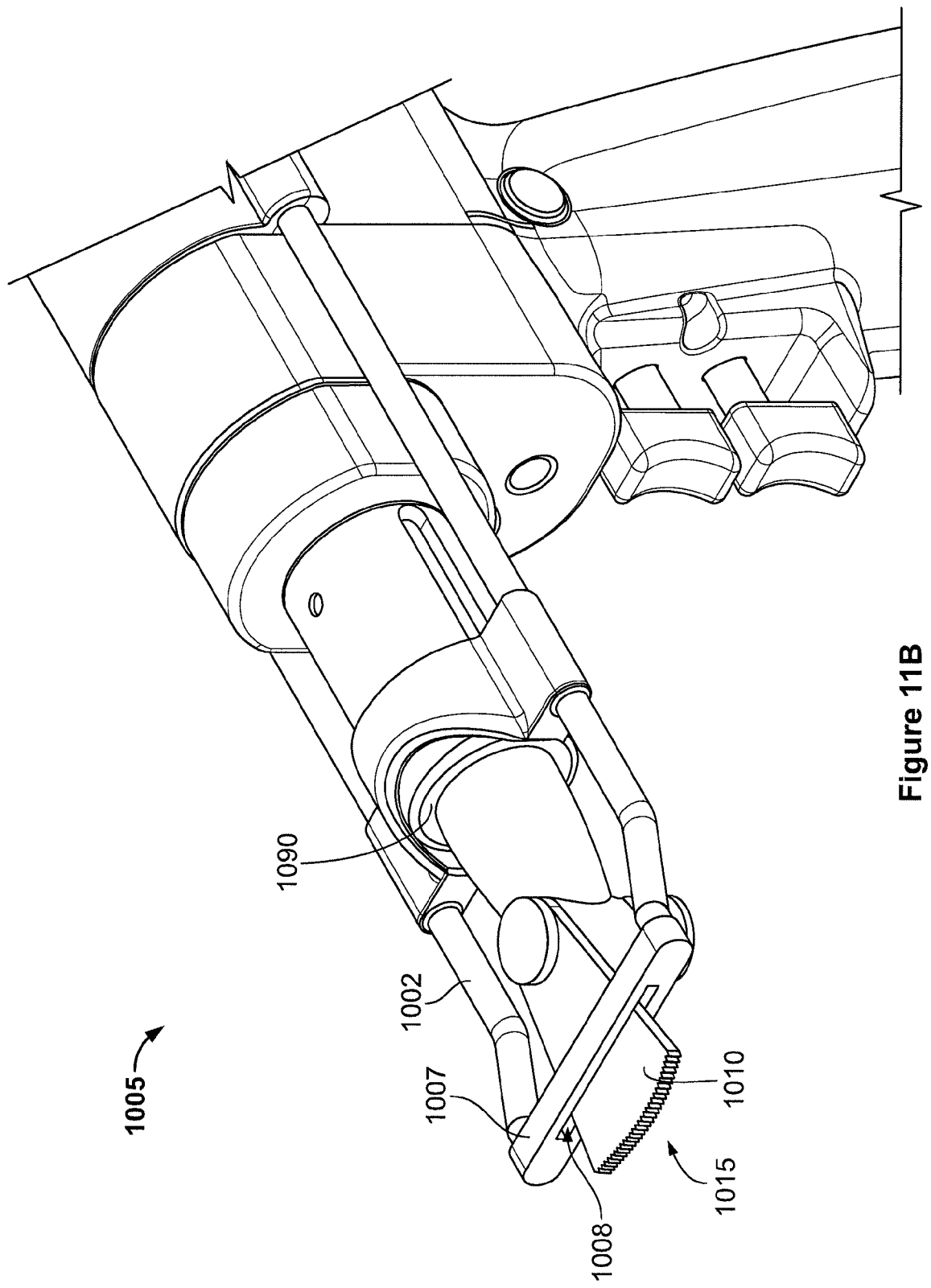

It should be appreciated that other medical devices can incorporate the metering and controlling features of the instruments as described herein. FIGS. 11A and 11B show an embodiment of an instrument 1005 having a working tool that is an oscillating bone saw blade 1010 coupled to chuck 1090 and surrounded by a saw blade guide 1007 that is coupled to a forward surface guide 1002 coupled to a rear surface guide 1000. The oscillating saw blade 1010 can have opposed proximal and distal ends and can be formed so that teeth 1015 extend forward from the distal end of the planar body of the blade 1010. The arrangement and geometry of the teeth 1015 can vary. The body of the blade 1010 can be formed of material such as stainless steel or other appropriate cutting material. The teeth 1015 can extend forward from the blade distal end through an elongate slot 1008 in the saw blade guide 1007 coupled to the instrument as best shown in FIG. 11B. The proximal end of the blade 1010 can include features (not shown) that facilitate the coupling of the blade 1010 to a chuck 1090. The chuck 1090 can connect to a drive mechanism that oscillates or reciprocates the saw blade 1010 to effect cutting. For example, the distal end of the blade 1010 can pivot back and forth relative to the proximal end of the blade 1010. As the saw blade 1010 saws through material, another drive mechanism can drive the rear surface guide 1000, the forward surface guide 1002 and the saw blade guide 1007 in an axial direction such that the body of the blade 1010 extends further through the slot 1008 of the saw blade guide 1007. The slot 1008 and the guides 1000, 1002, 1007 are configured such that they do not interfere with the oscillating and/or reciprocating motion of the blade 1010. The length of the blade 1010 can vary to accommodate various depth penetrations.

FIG. 12 shows an embodiment of an instrument 1105 having a working tool used to implant a Kirschner wire (k-wire) or other wire or pin. In an embodiment, the instrument 1105 can incorporate a wire driver 1110 used to implant a k-wire 1115 (or other wire or pin, hereinafter called "wire" for simplicity). The wire driver 1110 can be a modular attachment that can be used with the various instruments described herein. For example, the wire driver 1110 can be inserted into other instruments 10 described herein and used in place of the chuck 90, which can be removable. Alternatively, the wire driver instrument 1105 can be completely separate embodiments in which the wire driver 1110 is not modular or removable and instead is coupled permanently to the instrument 1105. It should be appreciated that the various instruments described herein can be modular such that mechanical features such as the chuck 90 or the axial drive motor 30 can be swapped out in place for one another.

The wire driver 1110 can hold the wire 1115 as well as rotate or oscillate the wire 1115. The wire driver 1110 can be released to slide axially to a new position causing more (or less) wire 1115 to be exposed for allowing a further penetration of the bone. In an embodiment, the body 1120 of the driver 1105 including the internal workings are cannulated such that the wire 1115 can be fed through the driver 1105 body 1120. The wire 1115 can extend through the cannulation in the body 1120 of the driver 1105 from the front of the driver 1105 out through the back end 1125 of the driver 1105. As mentioned, the wire driver 1110 can hold the wire 1115 in place much like a drill chuck. When the wire driver 1110 is activated, the rotational motor (not shown) can oscillate or rotate the wire 1115 in a clockwise or counter-clockwise direction. As with previous embodiments, the rotational motor can be biased in either rotational direction.

When the driver 1105 is activated the axial drive (not shown) can pull the surface guide(s) 1130 back (proximally) and the wire 1115 can advance into the work site such as bone. A trigger 1135 can be incorporated into the driver 1105 that holds the wire 1115 when grasped by a user. If pressure on the trigger 1135 is released, the trigger 1135 releases the wire 1115 such that the driver 1105 can slide forward or backward to expose less or more wire 1115, respectively. When a user desires more wire 1115, the trigger 1135 can be released and the driver 1105 pushes the surface guide 1130 forward. The length the surface guide 1130 moves forward equals the length of wire 1115 that is now available for advancement into the bone. This length can be added to the computed total axial distance as needed to obtain an accurate account of the length of wire 1115 that was driven into the bone. The wire 1115 can be held in place by either the guide 1130 (such as by pinching) or the bone into which the wire 1115 was driven can itself be used to hold the wire 1115 in place. If the wire 1115 is held in place by the bone, the user can urge the guide 1130 against the bone as the surface guide 1130 pushes the driver 1105 back to let out more wire 1115. If the user desires to remove the wire 1115 from the bone, the reverse axial drive (not shown) can be engaged such that the surface guide 1130 move forward and the driver 1105 moves backward away from patient while the trigger 1135 is engaged. It should also be appreciated that, although not shown, this instrument embodiment can incorporate a distal guide 170 coupled to a forward end of the surface guide 1130 as described in previous embodiments.

Tool Actuation

Actuation of the drive motors and other features of the instruments described herein can vary. Actuators can include triggers, buttons and switches that can be retracted, pressed, squeezed, slid or otherwise actuated to perform a certain function of the instrument 10. The actuators can be incorporated into a handle of the instrument 10 in such a way that is ergonomically comfortable for a user. For example, the instrument can include a pistol grip having trigger-type actuators such that the instrument 10 can be easily and comfortably held and actuated during use. It should be appreciated, however, that the instrument 10 can have other configurations such as a straight-bodied instruments that do not include a pistol grip.

Each drive motor can have a separate actuator for activation. For example, the drive motor 30 can be turned on by actuator 32 and the drive motor 60 can be turned on by actuator 62 (see FIG. 1). The actuators 32, 62 can be depressible triggers positioned on a handle 25 of the body 20, such as within a trigger housing 212. The actuators 32, 62 can adjust the speed of the drive motors 30, 60 in a manner that is proportional to the degree of depression of the actuators 32, 62, for example relative to the instrument handle 25. The direction the drive shaft 40 moves can be changed from a forward to a reverse direction, for example, by the position of a switch or other selectable mechanism. Similarly, the drive motor 60 can be made to move in a forward or reverse direction as determined by the position of a selectable switch. Further, the motor can be biased in either rotational direction.

In another embodiment shown in FIGS. 3-5, the instrument 10 can include a forward trigger 232 and a reverse trigger 234 that can each actuate both drive motors 30, 60. The forward trigger 232 can be a two-stage forward trigger 232 such that it can engage the rotational drive motor 60 in the first stage (i.e. effecting working tool 110 rotation) and the axial drive motor 30 in the second stage (i.e. effecting working tool 110 extension). The speed of the rotational drive motor 60 can be proportional to the degree of actuation of the first stage of the forward trigger 232, for example depression of the trigger 232. The speed of the axial drive motor 30 can be proportional to the degree of actuation of the second stage of the forward trigger 232. In an embodiment, the trigger 232 in the first stage can engage the rotational drive motor 60. The tool 110 spins and with further depression of the trigger 232 can reach full speed. Just before the trigger 232 enters the second stage, the axial drive motor 30 can engage. The axial drive motor 30 can cause withdrawal of the surface guides 300, 302 in a proximal direction P (see FIG. 4) to reveal a length of the working tool 110 allowing it to engage with and bore into the work as the user applies pressure to the instrument 10 and keeps it engaged with the work. It should be appreciated that the axial drive motor 30 can also cause the movement of the working tool 110 in a distal direction to reveal the length as described with respect to other embodiments herein. It should be appreciated that an axial force sensor can be incorporated that assists a user in keeping the instrument engaged with the work, as will be discussed in more detail below.

The reverse trigger 234 can cause both of the drive motors 30, 60 to reverse their direction. When the reverse trigger 234 is engaged while the two-stage trigger 232 is actuated during the first stage, the rotational drive motor 60 as well as the chuck 90 and the working tool 110, can spin in a reverse direction. When the second stage of the forward trigger 232 is actuated, and the reverse trigger 234 is still engaged, the rotational drive motor 60 as well as the chuck 90 and the working tool 110, can spin at maximal speed in a reverse direction and the axial drive motor 30 can begin to spin proportional to the degree of actuation of the second stage of the forward trigger 232. The action of the axial drive motor 30 can cause the drive lug 240, the rear surface guide 300, the forward surface guide 302 and the guide 170 to move in the distal direction (i.e. towards the work in direction of Arrow D, see FIG. 3). The axial movement of the guides 300, 302 can push the instrument 10 away from the work and draw the working tool 110 out of the work. In another embodiment, the motors 30, 60 can have independent reverse functions and can be controlled independently via independent actuators or triggers.

The instrument 10 can also include an oscillation select switch 262 (see FIGS. 3-5). The oscillating function can also be actuated by certain trigger combinations or an oscillation trigger. When the oscillation select switch 262 is in the "off" position, the instrument 10 can function as described above. When the oscillation select switch 262 is in the "on" position, the rotational drive motor 60 can oscillate in the appropriate direction when the triggers 232, 234 are actuated and the axial drive motor 30 function is not affected. If the forward trigger 232 is actuated, the instrument 10 can oscillate in the forward direction, i.e. the rotational drive motor 60 can oscillate forward but the axial drive motor 30 can cause the drive lug 240, the rear surface guide 300 the forward surface guide 302 and the guide 170 to move in a proximal direction as before. If the reverse and forward triggers 232, 234 are actuated, the instrument 10 can oscillate in the reverse direction, i.e. the rotational drive motor 60 oscillates in reverse but the axial drive motor 30 can cause the drive lug 240, the rear surface guide 300, the forward surface guide 302 and the guide 170 to move in the distal direction as before. The oscillation select switch 262 can affect the function of the rotational motor 60 not the axial drive motor 30. When selected it can cause the rotational motor 60 to oscillate.

Irrigation System

The instruments described herein can include an irrigation system. The irrigation system allows for the surgical field to be kept cool while the instrument 10 is in use and reduce the risk of tissue damage such as bone burning and bone death. The irrigation system can also reduce the risk of hardware failure, the need for re-operation, infection, limb loss and death. The irrigation system can include one or more irrigation nozzles 130 located at or near the engagement end 120 of the body 20. In one embodiment, the irrigation nozzles 130 spray fluid from the distal tip of the body 20. In another embodiment, the irrigation nozzles 130 can be routed internally through the working tool 110. The irrigation fluid can be sprayed through a channel running through the working tool 110 and exiting at a port near the distal end of the tool 110. In a further embodiment, the forward surface guide 302 can have one or more irrigation nozzles 130 (see FIGS. 3-5). The irrigation nozzles 130 can also be coupled to the distal guide 170.

The irrigation nozzles 130 can deliver irrigation fluid (i.e. a liquid or a gas) through irrigation tubing 340 (see FIGS. 3-5) from a sterile fluid bag or other irrigation fluid source. In an embodiment, carbon dioxide gas can be used to irrigate the work to remove heat. The irrigation tubing 340 can be coupled to the instrument 10 via an irrigation port near a proximal end of the body 20. The irrigation tubing 340 can be angled downward to avoid crimping and for more efficient manipulation of the instrument 10 by the user. An external fluid pump or gravity can be used to pressurize the irrigation system. The irrigation system can be kept outside the sterile surgical field except, for example, the irrigation tubing 340 connected to the instrument 10. Such an arrangement can contribute to the engagement end 120 and the working tool 110 remaining relatively free from bulk or other awkward equipment enabling more accurate placement and easy use of the instrument 10 in the surgical field. The irrigation system of the instrument 10 can also include a suction mechanism at or near the surgical field. Suction can be applied through the irrigation nozzles 130 or can be applied through additional channels.

The irrigation system can be controlled manually by the user such as with an irrigation actuator positioned, for example, on a handle 25 of the instrument 10 or by a foot pedal or other mechanism. The irrigation actuator can be a depressible trigger or button that can turn on or off the flow of irrigation fluid from the irrigation tube 340. The same actuator or another actuator can turn on or off the suction applied to the surgical field. The irrigation system can also be controlled automatically for example by one or more sensors near the work site communicating with an electronics package of the instrument to be described in more detail below. Automated irrigation is generally a desired option for users as it can effectively reduce drill bit temperature, bone temperature and the risk of bone burning.

Modularity and Internal Access

The body 20 of the instruments 10 described herein can include one or more removable covers that can be used to access one or more of the various internal components. Further, one or more of the internal components can be modular and can be completely separated from the body 20 of the instrument 10. This allows for interchanging parts as well as cleaning and sterilizing the components of the instrument 10.

In one embodiment, the instrument 10 can have a cover 122 near the engagement end 120 that can be removed to access, clean or remove the coupler 90, bearings 100 and drive shaft 80 and any other internal components of the instrument 10. The drive motor 60 can extend to a region near the distal end of the body 20 and allow for the actuation and release of the coupler 50. For example, the release can be a depressible button 52 (see FIG. 5) on a surface of the drive motor 60 that can allow a user to disconnect the drive motor 60 from the drive shaft 40 when the release is depressed to allow a user to remove the drive motor 60 from the body 20.

Figure 13:
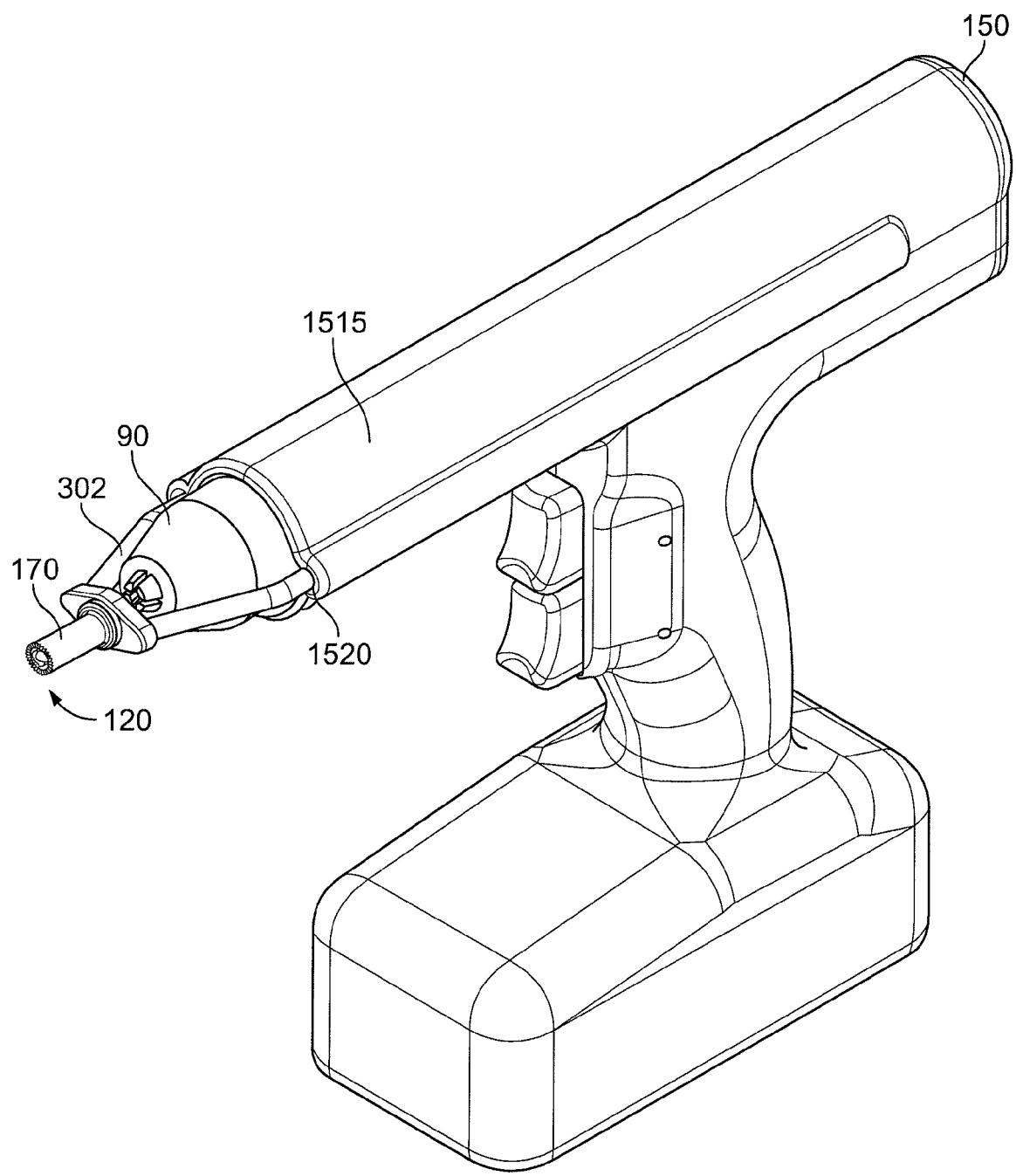
FIG. 13 is a perspective view of another embodiment of an instrument.

In another embodiment shown in FIG. 13, a body cover 1515 can enclose the rear surface guide (not shown) and at least a proximal portion of the forward surface guide 302. The forward surface guide 302 can be covered by the body cover 1515 up to the point where the chuck 90 is exposed at the distal engagement end 120 of the instrument 10 and can exit the body cover 1515 through openings 1520. These openings can include bushings seated around the perimeter of the opening 1520 that are sealed from the remainder of the instrument body.

The one or more body covers 1515 can be removed independently of one or more of the guides. Alternatively, the one or more body covers 1515 can be integrated with one or more of the guides such that they can be removed along with the covers 1515 in order to access the interior of the instrument 10. Proximally, the body 20 can include a removable end piece 150 that can be removed to gain access to the proximal region of the body 20 in order to clean or remove the modular portions of the instrument 10 near the proximal end, such as the drive shaft 40 and the drive motor 30. The removable end piece 150 can be incorporated with a removable electronics package as will be discussed in more detail below. One or more of the body covers can be translucent or transparent such that the components inside are visible from the outside without removal of the covers. It should also be appreciated that the components can be disposable and need not be removed or cleaned.

Electronics and Sensors

An electronics package 236 can be positioned within the body 20 of the instrument 10 and can have a variety of configurations. In an embodiment, the electronics package 236 can be positioned within the body 20 as well as within the handle 25. In an embodiment, the electronics package 236 can be positioned within a space of the body 20, for example near or at the proximal end behind drive motor 30 (see for example, FIG. 5 or 6). The electronics package 236 can include a display. The electronics package 236 and display can be removable along with one or more of the body covers. Information regarding the use of the instrument 10 can be relayed in real-time to the display such that the information is provided to a user instantaneously during use of the instrument 10, for example bore depth or other information as will be described in more detail below. The display can include an LED or other display using, for example, electrical filaments, plasma, gas or the like. The instrument 10 can also include a display that is not coupled or integrated within the instrument itself, for example, a heads-up display that communicates with the instrument 10 (i.e. either wired or wirelessly). The heads-up display can include a graphical user interface (GUI) that can display data and provide interactive functions such as a touch screen for input of data and information such as the drill bit size. The heads-up display can be mounted as is known in the art such as with a boom or other mechanism that provides user convenience. For example, the heads-up display can be mounted on a boom that can be easily positioned and moved around during a surgical procedure. The heads-up display can be autoclavable such that the display can be positioned within the surgical field where a user is using the instrument 10. Alternatively, the heads-up display can be inserted into a sterile cover such that the display can be positioned within the surgical field where a user is using the instrument 10.

The electronics package 236 (see FIGS. 5-6) can communicate with various sensors positioned within the instrument 10 that assess the status of the components of the instrument and communicate this information in real-time to the electronics package 236 and the user via a display. The instrument 10 can provide the user with alerts and information regarding the status of the instrument and instrument components during use such that manual and/or automatic adjustments can be made. The electronics package 236 can also include motor control electronics and software programs that can be programmed to automatically adjust the instrument 10 in real-time to maintain use of the instrument 10 within set thresholds. For example, the instrument can include software capable of being programmed to continuously measure and/or control a variety of functions including, but not limited to, bone depth, material strength, bone density, skive, drill bit development, speed of rotation, acceleration, deceleration, irrigation, voltage, torque, thrust, feed rate, current, voltage, axial movement, axial force and other functions of the instrument or a combination thereof. The instrument can include mechanical measurement systems, such as a mechanical torque measurement system as will be described in more detail below.

As such, the instruments described herein can detect and control penetration of the working tool through various tissue layers. The instruments can control, for example, axial feed rate, motor RPM, and engagement of the work to allow a user to avoid certain unsafe instrument situations. For example, the instruments described herein can detect joint penetration in real-time allowing a user to avoid "pop through" or plunging situations, for example, in which the instrument suddenly penetrates the cortical bone and inadvertently damages soft tissue or joint structures. Joint penetration can occur perpendicularly as well as tangentially (also known as skiving). The instruments described herein can provide an overall system stability that allows for the accurate tracking and detection and control of instrument status during use.

It should be appreciated that the control of the instruments described herein can also be adjusted manually by the user.

For example, the user can change the thrust of the drive motor 30 by letting up or pressing down on the actuator 32. The user can also change the thrust of the instrument 10 by pushing down or letting up on the axial pressure being applied to the instrument 10. In an embodiment, tissue resistance as compared to axial pressure on the instrument 10 applied by the user can cause/allow the relative position of the handle of the instrument 10 to feel as if it were backing out of the work as the tool 110 is axially extended from the instrument 10. This can require the user to apply additional axial pressure to drive the tool 110 through the tissue. The torque as related to the rotating tool 110 can also change during use of the instrument 10. This change provides feedback to the user who in turn can make appropriate adjustments to the axial and rotational movements as needed.

Figure 14:
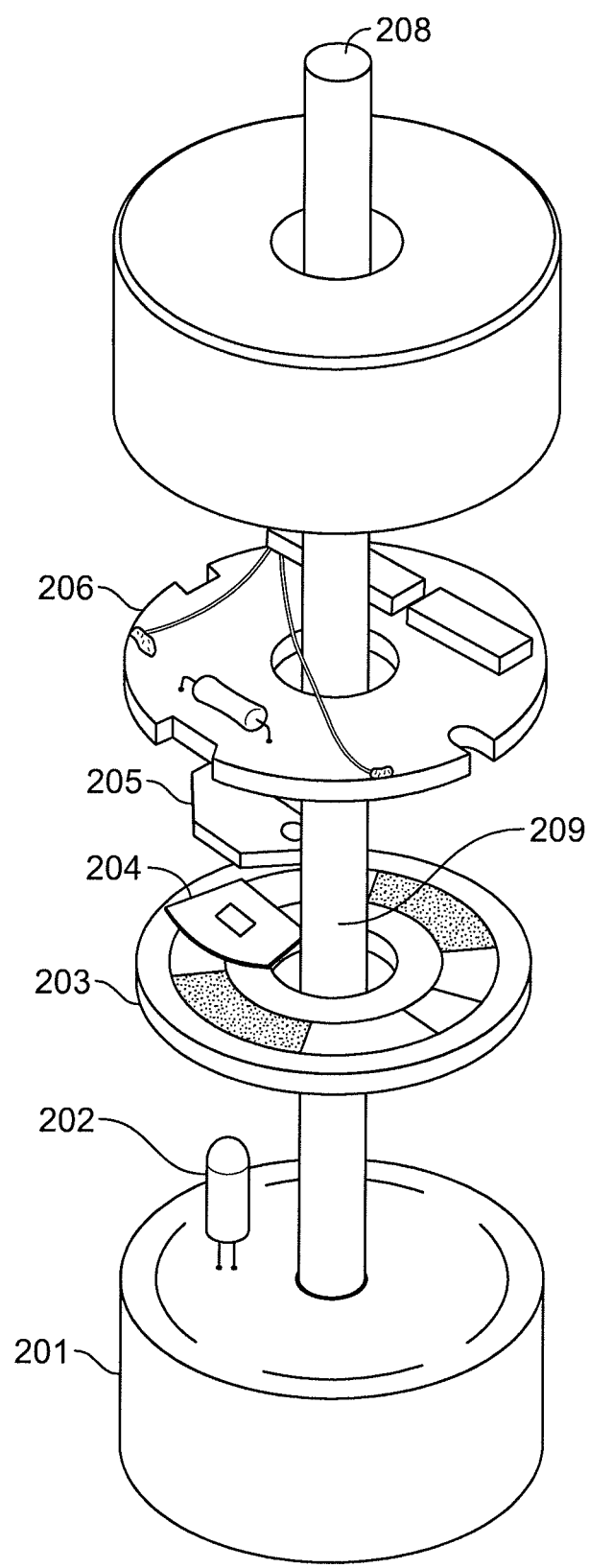
FIG. 14 is a perspective view of a rotary encoder for use with an instrument described herein.

The instruments 10 described herein can instantaneously measure the axial motion and the depth the working tool 110 travels into the work by a transducer or encoder, such as an incremental rotary encoder, an absolute rotary encoder, mechanical, magnetic, electrical, or optical rotary encoder, or the like (see for example BEI Optical encoder; www.motioncontrol-info.com/encoder_design_guide.html). The depth the working tool 110 travels into the work can also be measured by a synchro, a resolver, a rotary variable differential transformer (RVDT) or a rotary potentiometer, or the like. As shown in FIG. 14, the rotary encoder 39 can include a bearing housing assembly 201, a light source 202, a code disc 203, a mask 204, a photodetector assembly 205, an electronics board 206 that rotate around shaft 208. In an embodiment, the rotary encoder is an incremental rotary encoder with dual channels in quadrature with an additional data track to provide an internal position reference for setting a "zero point". The rotary encoder can be an absolute rotary encoder.

The encoder can measure rotation and convert that information into axial motion. The encoder can interface with the drive motor 30 and the drive shaft 40 and can provide instantaneous information on the position of the drive shaft 40 regarding the depth of axial movement of the working tool into a bore. This information can be fed to the electronics package 236 that can perform count multiplication to determine the tool position. For example, the rotation of the drive shaft 40 can be measure and a calculation performed to determine the distance traveled. This distance traveled can be compared to a set point or zero point such that the position of the working tool 110 from the distal end of the instrument can be calculated. This calculation relates to depth as determined by the position of the distal end of the instrument with respect to the target tissue (e.g. bone).

In an embodiment, the instrument can include a meter that measures the rotational speed (see for example the speed device described in U.S. Pat. No. 4,723,911), time, velocity, acceleration, deceleration or torque. The meter can provide the user information pertaining to the passage of the working tool 110 through different layers of tissue. For example, movement of the working tool 110 through cortical bone into medullary canal or cancellous bone, medullary canal or cancellous bone to cortical bone, or from cortical bone to soft tissue. In an embodiment, metrics can be obtained via an axial force sensor and/or a torque sensor to measure drive or motor torque directly. In an embodiment, the rotational drive motor 60, or a gearbox connected to the rotational motor 60, can be positioned such that it can press against a force sensor to provide direct measurements of torque that can be displayed to a user and provide information pertaining to the passage of the tool through varied layers of tissue.

In another embodiment the rotational drive motor 60 can have a torque sensor (not shown). In an embodiment the rotation drive motor 60 can be a brushless DC (BLDC) electric motor having one or more Hall sensors. When the tool passes from cortical bone into medullary canal or cancellous bone or from cortical bone into soft tissue the measured torque can drop dramatically. The information can be relayed to the display 236 and integrated with the function of the motor drivers and their actuators. For example, in an embodiment, when the tool 110 is moving axially in a forward direction and passes from cortical bone to medullary canal or cancellous bone or from cortical bone to soft tissue the reduced torque will interrupt the axial motion. The axial drive can then be reengaged by releasing pressure on the forward two-stage trigger and reapplying pressure.

The instruments 10 described herein can also control the depth of penetration of the working tool 110. In an embodiment, the maximum depth of the bore that is to be created by the instrument 10 can be programmed with electronics in advance of drilling. The measurement can be zeroed by the user prior to use, for example, by depressing an axial measurement selector/reset button. This allows the user to zero the measurement according to the length of the selected tool 110. In one embodiment, the distal end of the working tool 110 can be aligned with the distal end of the body 20 and the instrument zeroed. This can be performed manually by the user or electronically with set points and a feedback system (i.e. interface with the coupler). The alignment of the distal end of the tool 110 and the distal end of the body 20 can be such that the two are flush with one another or the distal end of the tool 110 can be some distance beyond the distal end of the body 20, for example between about 3 mm and 7 mm. The tool 110 can be positioned flush against the bone prior to drilling. As the tool 110 advances into the bone, the instrument 10 can be held flush against the bone. The instrument 10 can also include a distal guide 170 and be zeroed once the tool 110 aligns with the distal end of the guide 170 (and a fixation plate attached to the guide 170, if present). Once the cut is started and the tool 110 can be flush with the bone, the user can use the axial drive to further advance the tool 110 through the bone. The electronics package 236 can be zeroed as described above to include the additional axial length of the guide 170.

In another embodiment, the user can feed in a distal direction a portion of the working tool 110, for example 30 mm if working on a tibia or femur or 12 mm if working on a radius. The user can then manually drill through the bone as with an axially static drill. Upon reaching that pre-programmed depth, if the distal cortex had not yet been breached, the axial drive can be used to penetrate the bone further. In another embodiment, the electronics can contain a preset maximum distance that can limit the distal travel of the tool 110. For example, a stop and go signal (i.e. single click of the trigger) or a double stop and go (i.e. double click of the trigger) can release the depth stop and allow further travel. Any of a variety of schedules can be programmed into the electronics to control distal advancement of the tool. For example, each time the tool 110 is advanced beyond the initial stop, the electronics can be programmed to allow only a further distal travel of for example 3 mm or 6 mm or other incremental distance before stopping again and alerting the user similar to a snooze alarm system of a clock radio.

Identifying the desired depth of penetration for pre-programmed embodiments can be determined, for example, by knowing the typical size of the target tissue based upon the age and size of a patient or the actual size of the target tissue from pre-op radiographs, CT scans or MRI scans. A user can also manually estimate to approximately 70-80% depth travel through the proximal cortex, the medullar bone and close to or into the distal cortex prior to the automatic pre-programmed settings taking effect. For example, the user can manually estimate until a region of the bone is entered where a greater amount of control is desirable such as the distal cortex. At that stage, the axial drive of the instrument can be used to slowly proceed through that portion of the bone to the target location. A user can also proceed until a pop is felt or a change in speed can be heard in the drill. This can be augmented by acceleration or torque measurements provided to the user. For example, as the drill bit penetrates to the very last layers of the distal cortex it can begin to accelerate with a burst of acceleration as it breeches the distal cortex completely, this can also be sensed as a change in torque. In another embodiment, the RPM of the rotational drill motor is kept constant, preventing tool acceleration or deceleration. This allows the torque to be correlated to material strength. The instrument can provide its own auditory output to accentuate the sometimes subtle auditory changes caused by the drill bit. Upon reaching the predetermined target depth, axial movement of the device can automatically slow or stop while rotational movement can continue. It should be appreciated, however, that the user can manually override any pre-programmed limitations or automated controls by actuation/triggers on the device without changing hand positions to continue.

As described above, the instruments described herein can include one or more sensors that communicate information to the user using a variety of alert mechanisms and/or graphical displays. In an embodiment, the instrument includes an axial force sensor and an axial force alert. As described herein, the axial force sensor can be used to sense the axial force applied at the distal end of the drill guide and/or applied by the working tool. The axial force sensor can communicate with the axial force alert and provide information to the user to ensure that the distal end of the drill guide and/or tool stay engaged with the work and maintains an appropriate level of pressure. Applying too much pressure or force on the work can increase the risk for damage to the work or surrounding tissues. Applying too little pressure or force can cause the tool to back off the work and prevent tool advancement at the desired rate. The axial force sensor can communicate with the axial force alert in real-time to provide the user with information regarding the status of the drill guide and whether the applied axial force is at the desirable pressure for an optimum result. The axial force alert can include an alarm or other auditory signal, a light or other visual signal, a vibration or other tactile signal, or a combination thereof. In an embodiment, the visual output can be an LED light or graphical interface positioned in the line of sight with the work, for example near or at the proximal end or back of the device. The output of the axial force alert can be proportional to the axial force being applied. For example, the axial force alert can include a light that can change color or a plurality of lights that sequentially illuminate depending on the axial force applied. Alternatively, the axial force alert can include an auditory alert that changes pitch or frequency depending on the axial force applied.

In use, the user can inadvertently lighten manually applied forward (or axial) pressure on the instrument 10 that can result in a slowing of progress into the work and consequently the drill guide from backing away from the work. A user can maintain forward pressure on the instrument 10 such that the working tool 110 drives into the bone distally as the guides retract in a proximal direction. If a user does not maintain forward pressure the instrument 10 can be pushed in a proximal direction resulting in the working tool 110 not moving into the work. It can be desirable, however, to use as little forward pressure on the instrument as necessary to avoid injury to the bone. In some embodiments, the instrument 10 can include an axial force sensor that can measure the axial force a user applies to the work. The axial force sensor can interact with the electronics and provide an output to the user (e.g. visual or auditory or other output) to indicate when an amount of pressure is being applied by the user. The instrument can be programmed to provide the output to the user when an appropriate amount of pressure is being applied or when the pressure being applied falls outside a programmed range. In one example, LED lights can be positioned near a proximal end of the instrument within a user's line-of-sight such that the axial force applied can be visualized. For example, a flashing white LED can mean too little axial pressure is being applied, a green LED can mean the axial pressure is in a desired range and a flashing red LED can mean the axial pressure is too high.

The instruments described herein can also include a torque sensor that detects the torque applied by the rotational motor and a torque alert. As described previously in reference to the axial force alert, the torque alert can also include an alarm or other auditory signal, a light or other visual signal, a vibration or other tactile signal, or a combination thereof. For example, the sensed torque similar to the sensed axial force can be displayed visually such as on a graphical interface in the line of sight with the work. The torque alert can also be proportional relative to the torque being applied. Further, the output for the axial force alert can be distinguishable from the output for the torque alert. For example, a first auditory signal can be provided by the axial force alert proportional to the axial force and a second auditory signal can be provided by the torque alert proportional to the torque applied. The auditory signals from the two alerts can be distinguishable by the user as being separate. For example, the axial force alert can be a different pitched auditory signal compared to the torque alert. In another embodiment, the axial force alert can signal the user only when conditions at the work change, whereas the torque alert can be a continuous signal, such as a sound with a variable pitch that is proportional to the torque or energy being sensed. It should be appreciated that any number of sensors and a variety of alerts or graphical information can be used singly or in combination as is known in the art.

The systems described herein can also provide information to the user regarding optimal screw placement even in the case of a shared or convergent drill hole for the placement of interference screws, such as screws that are purposefully touching. Clinically, a user can feel when an interference screw is contacted by a drilling or driving device. However, once the interference screw is engaged the distal cortex can no longer be clinically felt by the user and a myriad of potential problems exist with regard to injury of distal structures. Both the interference screw and the distal cortex can be detected by tracking changes in the metrics, for example current or measured torque. The data can be used to inform the user in real-time when the instrument is in contact with one or more of the bone cortices or the screw. Similarly, the instruments described herein can provide instant, intra-operative feedback on drill bit performance such as drill flute clogging and the assessment of drill bit sharpness using a calibration block.

Material strength and bone density can be determined by comparing intraoperative metrics such as current, measured torque or axial force with existing empirical data obtained while drilling with known drill bit sizes, drill bit types, axial feed rates and motor RPMs. The instruments described herein therefore can be useful in diagnosing bone pathologies such as osteoporosis and the detection of holes or fractures in the bone being drilled. Further, material strength and bone density data can assist a user in choosing an appropriate fixation technique, e.g. non-locking (cortical or cancellous) versus locking (unicortical or bicortical). Conventionally, to select the appropriate fixation technique a user must make an educated guess or using bone density data obtained prior to the fracture to estimate local material strength at the fracture fixation site. For example, dual energy X-ray absorptiometry (DEXA) scans are commonly used to measure bone density and monitor osteopenia or osteoporosis treatments. But a DEXA scan cannot be performed acutely for a fracture patient and the standardized regional measurements may not be relevant at the fracture site. The instruments described herein provide an advantage in that determination of bone strength and bone density can be performed in acute situations and in real-time at the fracture site.

Drilling torque (or energy) of the working tool is related to the properties of the bone, such as its material strength and its bone density. One or more of the sensors described herein can be used to estimate the material strength and bone density such that the instrument can detect transitions between different types of bone, as well as entry and exit from bone in real-time.

Figure 15:
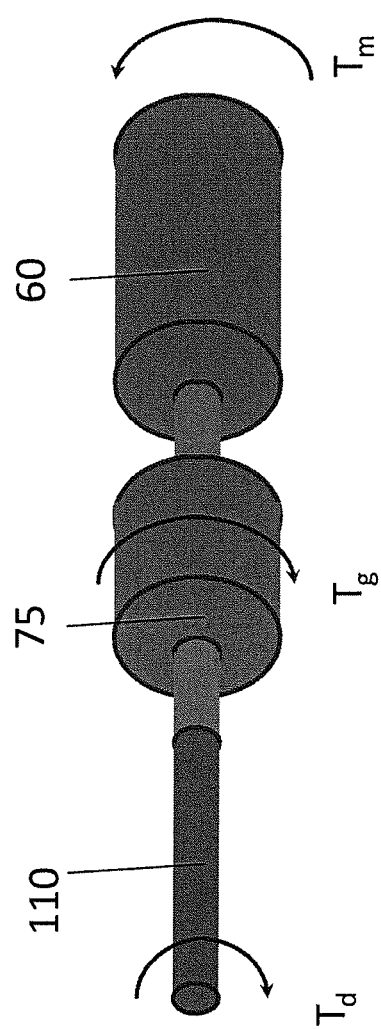
FIG. 15 is a schematic view of a drive mechanism showing torque forces generated by a working tool, gearbox and motor.

As shown in FIG. 15, a motor 60 can rotate and produce a motor torque $T_m$ that is in the direction of rotation of a working tool 110 coupled to the motor 60. Drilling torque $T_d$ is opposite the direction of rotation of the working tool 110. A gearbox 75 can be incorporated in the instrument to convert the high-speed, low-torque operation of the motor 60 to a higher torque working tool 110 speed. The gearbox 75 can exhibit an additional torque component $T_g$ due to internal energy losses, such as mechanical losses in the form of drag that counteracts torque and can result in a loss of energy between the motor 60 and the working tool 110. Gearbox torque $T_g$ is also opposite the direction of rotation of the working tool 110. The motor 60 can be held as the reference point and the motor torque $T_m$ measured electronically. In this embodiment, the instrument measures the current required to operate the motor 60, for example a brushless DC motor with a Hall Sensor that operates a drive train, and the motor 60 acts as both the actuator and the sensor. Motor torque measurements in this embodiment include both drilling torque $T_d$ and gearbox $T_g$ losses. The gearbox inefficiencies can affect the accuracy of the torque measurements. The error in estimating the drilling torque component can be more pronounced for larger gear ratios in that more gears have more surface contact and thus, more drag.

Figure 16:
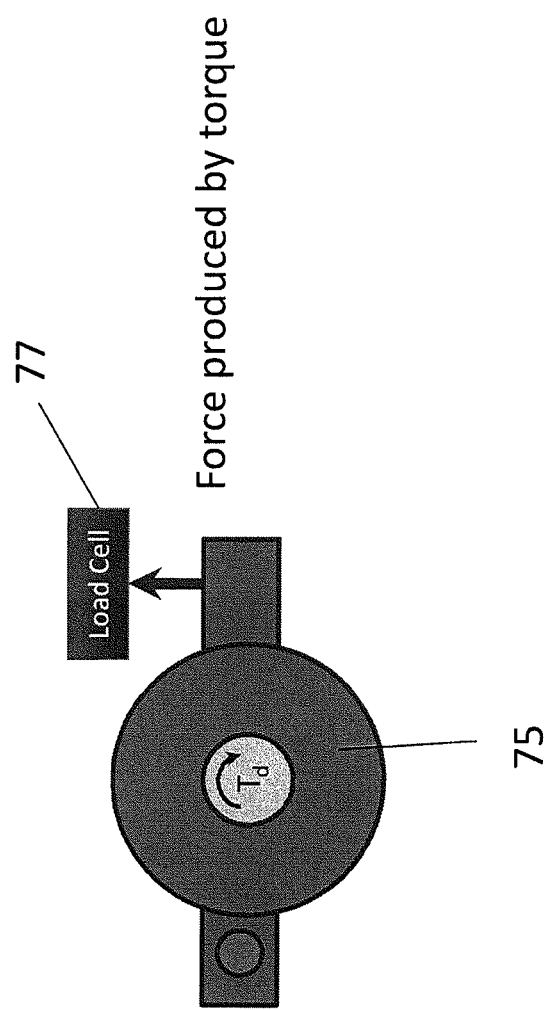
FIG. 16 is a schematic view of a direct torque sensor measuring force produced by drilling torque.

In another embodiment, the instrument can directly measure torque (see FIG. 16). The gearbox 75 is held as a reference point for the torque measurement and only the drilling torque $T_d$ is measured. Measurements of the drilling torque $T_d$ can be taken at the output of the gearbox 75 such that internal gearbox losses are not included in the torque measurement although the motor 60 may still drive against the internal drag. A discrete sensor can be incorporated in the instrument to convert the drilling torque $T_d$ into a measurement signal. A mechanical beam or level can be incorporated to support the gearbox 75 and convert the torque $T_d$ into a linear force. The linear force can be converted into an electrical signal using a strain gauge load cell or scale or other torque sensor 77 to measure the resulting linear force. The direct torque measurement does not measure the energy lost internally to the gearbox 75 or the other motor components. The motor 60 can exert torque between its shaft and housing, which can be rigid mounted to the gearbox 75. In this embodiment, the torque required to overcome the internal losses of the gearbox 75 can be transferred through the housing of the motor 60 and gearbox 75 and the mechanical path does not include a torque sensor. The torque sensor 77 can, instead be positioned between the gearbox housing 75 and the working tool 110 by attaching the torque sensor 77 to the drill housing. The user can hold the body 20 of the instrument 10, which is rigidly attached to the gearbox housing 75.

Although motor self-torque measurement can be more convenient since no additional sensor is needed, the accuracy can be lower than for a direct torque measurement in which a torque sensor is used. Direct torque measurements from a manufacturing standpoint can also allow one to design the gearbox independently from the torque measurement sensitivity.

The instrument 10 can be a corded or cordless powered instrument. In an embodiment, the instrument 10 includes and is powered by a removable battery 360 (see FIG. 5). The battery 360 can be enclosed within a battery cover 362 capped on the bottom by a battery case cover 364. The body 20 can accept battery release buttons 366. The battery 360 can have different chemical compositions or characteristics. For instance, batteries can include lead-acid, nickel cadmium, nickel metal hydride, silver-oxide, mercury oxide, lithium ion, lithium ion polymer, or other lithium chemistries. The instruments can also include rechargeable batteries using either a DC power-port, induction, solar cells or the like for recharging. Power systems known in the art for powering medical devices for use in the operating room are to be considered herein.

Methods of Use

Below is an example of a method of using an instrument described herein. It should be appreciated that a variety of driving devices or working tools can be coupled to the instruments described herein. Description related to guides on a drilling device having a drill bit coupled thereto is not intended to be limited to only drills and drilling bores. Rather, the instruments and guides can be used to saw or drive into tissues as described herein.

It should be appreciated that any of the instruments described herein can be coupled to robotic arms or robotic systems or other computer-assisted surgical systems in which the user uses a computer console to manipulate the controls of the instrument. The computer can translate the user's movements and actuation of the controls to be then carried out on the patient by the robotic arm. Robotics can provide real-time pre- and inter-operative tactile and/or auditory feedback along with visualization, such as three-dimensional modeling. The robotic system can have an articulated endowrist at the end of two or more "working" arms configured to be inserted through a small portal. A stable, camera arm with two lenses (allowing stereoscopic images) can be also inserted through another small portal. The end-effectors can manipulate instruments and can have various degrees of freedom. The user can control the robot through a console placed in the operating room, allowing control of both the external and internal surgical environments. The user's interface can have instrument controllers that can filter tremor and decrease the scale of motion. Foot pedals can expand the user's repertoire, allowing tissue coagulation and irrigation. Visual feedback can be through a stereoscopic display. Robotic systems to which the devices disclosed herein can be coupled include the Haptic Guidance System or RIO® Systems (MAKO Surgical Corp, Ft. Lauderdale, Fla.) and the da Vinci® Surgical Systems (Intuitive Surgical, Sunnyvale, Calif.). Other surgical robots can be considered as well including the Robot-Assisted Micro-Surgery (RAMS) system (MicroDexterity Systems, Inc.), NeuroArm® (University of Calgary), Zeus® Surgical robots, SpineAssist (Mazor Surgical Technologies, Israel), ROBODOC and ORTHODOC (Curexo Technology Corp., Fremont, Calif.), ACROBOT (Acrobot, Elstree, UK), PathFinder (Prosurgics Ltd., Loudwater, High Wycombe, UK), and Laprotek system (Hansen Medical, Inc.). Other robotic arms can be used with the instruments described herein such that the instrument can be independently controlled by the robot as opposed to direct manipulation by the user.

In one embodiment of the method, the user can dissect tissue down to the bone and create a field large enough to put against the bone the working tool 110 or distal guide 170 or an implant attached to the distal guide 170. Screws can be placed across fractures without any other implants or a plate can be fixed across the fracture by bone screws. The screws can lock into the plate and bone. When a plate is to be used, the user can create a field large enough to place the plate. Alternatively, the plate can be inserted through a small incision such that the user can slide it along the surface of the bone in combination of blunt dissection of the tissue along the way (i.e. subcutaneous plate). The screws can be placed, for example using a radiograph to find the holes in the plate, through small incisions through the skin with dissection down to the bone. The surrounding tissue can be protected using retractors, a guide through which the working tool is inserted, attachable guides placed on the instrument and the like. If a distal guide 170 is used, the length of the guide 170 can be accounted for in the depth measurement. If a guide 170 attached to an implant is used, the depth can be automatically or manually zeroed. For example, if a plate is used the thickness of the plate can be automatically or manually accounted for in the zeroing.

The working end of the instrument 10, with or without a distal guide 170, can be placed next to the exposed and dissected bone and the instrument zeroed. Alternatively, the user can extend a few millimeters of the working tool 110 to engage the bone and drill a counter-sink or pilot hole prior to zeroing the instrument 10. Where a fixation plate is used, the plate can be placed next to the bone and the drill end placed snug to the plate. Alternatively, some plates have guides that interface such that the instrument is directed at a selected angle. The instruments disclosed herein can be made such that they attach to or freely engage these types of distal guides 170.

The user can apply pressure axially and engage first the rotational drive motor 60 to the desired speed. The user can proceed to engage the axial drive motor 30 either continuously or incrementally, depending upon the material strength and bone density and preference of the user. The drilling can continue through the cortical bone, through the medullary canal or cancellous bone, into and through the distal cortical bone. Once through the distal cortical bone as determined by pre-set depth control mechanism, axial resistance, auditory feedback from the rotational speed of the drill bit and/or auditory feedback from acceleration or torque sensors, the axial movement can be stopped. The user can remove the working tool 110 by reversing the axial drive motor 30 or by pulling back on the instrument 10. The rotational drive motor 60 can be left engaged and in the forward direction to facilitate clearing the hole created. The user can read the depth on the display 236 and select the proper screw for implantation. The screw can be implanted using a screw driver or the like. In another method, the user can perform a unicortical procedure wherein the working tool is stopped prior to some other endpoint such as before or after a growth plate or before or after the distal cortex.

In use, an instrument 10, such as the instrument shown in FIG. 4, can be set against exposed bone or, if used, the fracture fixation plate or other type of implant such as a joint prosthetic. The appropriate zero-depth position can be determined automatically. Once the user activates the trigger 232, the guide 170 as well as the guides 300, 302 retracts in the proximal direction (arrow P) and the working tool 110 can extend through the guide 170. The working tool 110 can engage the work and bore into the work as the user applies pressure to the instrument 10 and keeps it engaged with the work. The working tool 110 can drill into the bone by the amount the guide 170 retracts. The guide 170 retraction can be measured instantaneously and shown on a display, for example a display positioned at the back of the instrument 10. The automatic determination of the zero-position whether set against bone or against a fracture fixation plate can depend upon algorithms related to the way the guide 170 sets against the bone or the plate and the thickness of the plate. These variables can be unique to each plating system and set of guides. The depth of the travel of working tool 110 into the work, and/or the instantaneous torque or torque curve, can be measured and shown on the display 236 simultaneously and instantaneously as the working tool 110 moves axially in a distal direction and penetrates the work.

Once the desired depth of penetration is reached, the reverse trigger 234 can be actuated to cause both of the drive motors 30, 60 to reverse their direction. The action of the axial drive motor 30 can cause the drive lug 240, the rear surface guide 300, the forward surface guide 302 and the guide 170 to move in an axial direction away from the body 20 of the instrument 10 in a distal direction such that the axial movement pushes the instrument body 20 away from the work and draws the tool 110 out of the work. Alternatively, the operator can pull the tool 110 from the work with the instrument either on (in any direction) or off.

Aspects of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device. For example, a software program can be incorporated into the device that takes advantage of the reproducible relationship between current, torque, material strength and density in a system where the RPM of the rotational motor is held constant. Current is proportional to torque and torque is proportional to bone strength and density. As such the software can correlate the current the motor uses during drilling or sawing to the material strength and bone density. Such a software program can be used to measure material strength and bone density in real-time by reading the current being used by the motor. The software program can also be used to control RPM, feed rate, current and/or voltage.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

While this specification contains many specifics, these should not be construed as limitations on the scope of the claims or of what can be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. For example, a current sensing mechanism can be incorporated into a drill or saw device and used independently of a depth-control mechanism. Similarly, a depth-control mechanism can be incorporated into a device that does not include other sensing mechanisms. Moreover, although features can be described above as acting in certain combinations and even initially claimed as such, one or more features from a claimed combination can in some cases be excised from the combination, and the claimed combination can be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A medical driving device comprising:
   a housing having a proximal end and a distal end and a hand-held portion near the proximal end of the housing;
   a first drive shaft extending through a region of the housing between the proximal and distal ends;
   a first motor coupled to a region of the first drive shaft;
   a second motor coupled to a second drive shaft;
   a coupler coupled to the second drive shaft, wherein the coupler is interchangeably connected to a working tool;
   a tool guide assembly coupled to the housing, the tool guide assembly comprising:
      a tool guide surrounding the working tool; and
      a surface guide having a proximal region and a distal region, the distal region configured to couple to the tool guide and the proximal region configured to couple to the first motor,
      wherein the first motor causes axial motion of the tool guide assembly towards the proximal end of the housing to a retracted state upon actuation and drives a length of the working tool into a target region of a bone;
   a torque sensor configured to sense torque in at least the second motor by continuously measuring current used to drive the second motor to sense in real-time a change in torque; and
   a programmable electronics package programmed to keep constant rotations per minute (RPM) of the second motor preventing working tool rotational acceleration or deceleration, and programmed to integrate over time the sensed torque from the torque sensor to obtain energy, which correlates to material strength of work penetrated.

2. The device of claim 1, wherein the first drive shaft and the second drive shaft are in a co-axial arrangement relative to one another.

3. The device of claim 1, wherein the first drive shaft and the second drive shaft are in a parallel arrangement relative to one another.

4. The device of claim 1, wherein the first drive shaft and the second drive shaft are in an orthogonal arrangement relative to one another.

5. The device of claim 1, wherein the hand-held portion further comprises an actuator.

6. The device of claim 1, wherein the second motor coupled to the second drive shaft drives the coupler and the working tool.

7. The device of claim 6, wherein the coupler and the working tool are rotated by the second drive shaft.

8. The device of claim 1, wherein the device is functionally coupled to a robotic arm.

9. The device of claim 1, wherein the working tool is selected from the group consisting of a drill bit, a detuned drill bit, wire, Kirschner wire, pin, trochar, burr, screwdriver, reamer, saw, saw blade, router, router bit, stepped drill bit, bone plug removal tool, bone harvesting tool, bone marrow harvesting tool, and bone marrow aspirating tool.

10. The device of claim 1, wherein the torque sensor is positioned on the housing between the second motor and the working tool, wherein the torque sensor is configured to directly measure torque of the working tool.

11. The device of claim 10, wherein the torque sensor is configured to communicate measurements of torque to the programmable electronics package.

12. The device of claim 11, wherein a change in the measurements of torque corresponds to change in material strength and density of work penetrated.

13. The device of claim 12, wherein the work penetrated comprises medullary canal, cancellous bone, cortical bone, or soft tissue.

14. The device of claim 12, further comprising an alert, wherein the torque sensor communicates with the programmable electronics package in real-time and the alert provides a user with information regarding status of the driving device during use.

15. The device of claim 14, wherein the alert comprises an auditory, visual or tactile signal.

16. The device of claim 1, further comprising one or more axial force sensors configured to sense the axial force applied at one or both of the distal end of the tool guide and the working tool.

17. The device of claim 16, further comprising an axial force alert, wherein the axial force sensor communicates with the programmable electronics package in real-time and the axial force alert provides a user with information regarding status of the driving device during use.

18. The device of claim 17, wherein the axial force alert comprises an auditory, visual or tactile signal.

19. The device of claim 18, wherein the visual signal comprises one or more LEDs positioned within a user line-of-sight, wherein the LEDs indicate degree of axial pressure being applied by the user in real-time.

20. The device of claim 1, further comprising a gearbox connecting the second motor to the working tool.

21. The device of claim 1, wherein the tool guide surrounding the working tool is configured to assist in the engagement of an implant.

22. The device of claim 21, wherein the tool guide comprises one or more features that mechanically couple with corresponding features of the implant.

23. The device of claim 21, wherein the implant comprises a fracture fixation plate or a joint part.

24. The device of claim 21, wherein the tool guide couples to the implant at an angle away from perpendicular.

25. The device of claim 1, wherein a change in current used to drive the second motor is received by the programmable electronics package signaling when to stop the axial motion of the tool guide assembly and preventing penetration of the working tool beyond the target region of the bone.

26. The device of claim 1, wherein the surface guide comprises a forward surface guide and a rear surface guide, wherein a distal region of the forward surface guide couples to the tool guide and a proximal region of the forward surface guide couples to the rear surface guide, and wherein the rear surface guide couples to the first drive shaft.

27. The device of claim 26, wherein the rear surface guide is attached to a drive lug coupled to and powered by the first motor to move the rear surface guide in an axial direction.

28. The device of claim 26, wherein the forward surface guide comprises at least two supports that mate with corresponding supports of the rear surface guide.

29. The device of claim 26, wherein the forward surface guide engages an outer surface of the coupler.

* * * * *